(12) United States Patent
Childers et al.

(10) Patent No.: US 7,932,098 B2
(45) Date of Patent: Apr. 26, 2011

(54) MICROFLUIDIC SYSTEM UTILIZING THIN-FILM LAYERS TO ROUTE FLUID

(75) Inventors: Winthrop D. Childers, San Diego, CA (US); Paul Crivelli, San Diego, CA (US); David Tyvoll, La Jolla, CA (US); James A. Feinn, San Diego, CA (US); Douglas A. Sexton, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1820 days.

(21) Appl. No.: 10/286,314

(22) Filed: Oct. 31, 2002

(65) Prior Publication Data
US 2004/0086427 A1 May 6, 2004

(51) Int. Cl.
*G01N 27/26* (2006.01)
*G01N 1/10* (2006.01)

(52) U.S. Cl. ........ 436/180; 436/174; 436/175; 436/176; 436/177; 436/178; 436/179; 436/181; 422/57; 422/100

(58) Field of Classification Search ............. 436/174, 436/175, 176, 177, 178, 179, 180, 181; 422/57, 422/100
See application file for complete search history.

(56) References Cited

U.S. PATENT DOCUMENTS

| | | | |
|---|---|---|---|
| 5,376,252 A | 12/1994 | Ekstrom et al. | |
| 5,498,392 A | 3/1996 | Wilding et al. | |
| 5,587,128 A | 12/1996 | Wilding et al. | |
| 5,699,157 A | 12/1997 | Parce | |
| 5,779,868 A | 7/1998 | Parce et al. | |
| 5,800,690 A | 9/1998 | Chow et al. | |
| 5,824,204 A | 10/1998 | Jerman | |
| 5,842,787 A | 12/1998 | Kopf-Sill et al. | |
| 5,846,396 A | 12/1998 | Cherukuri et al. | |
| 5,856,174 A | 1/1999 | Lipshutz et al. | |
| 5,858,187 A | 1/1999 | Ramsey et al. | |
| 5,880,071 A | 3/1999 | Parce et al. | |
| 5,885,470 A | 3/1999 | Parce et al. | |
| 5,922,591 A | 7/1999 | Anderson et al. | |
| 5,955,029 A | 9/1999 | Wilding et al. | |
| 5,958,203 A | 9/1999 | Parce et al. | |
| 5,958,694 A | 9/1999 | Nikiforov | |
| 5,965,410 A | 10/1999 | Chow et al. | |
| 5,976,336 A | 11/1999 | Dubrow et al. | |

(Continued)

FOREIGN PATENT DOCUMENTS

WO  WO 99/19717  4/1999

OTHER PUBLICATIONS

Julia Khandurina et al, "Bioanalysis in Microfluidic Devices", Journal of Chromatography A, vol. 943 (2), Jan. 18, 2002, pp. 159-183.

*Primary Examiner* — Krishnan S Menon
*Assistant Examiner* — Rebecca Fritchman

(57) ABSTRACT

Systems, including apparatus and methods, for microfluidic processing and/or analysis of samples. The systems include a microfluidic device having a substrate and a thin-film layer formed on the substrate. The thin-film layer may be included in electronics formed on the substrate. The electronics may provide electronic devices configured to sense or modify a property of the sample. The thin-film layer defines an opening for routing movement of fluid and/or sample within the device.

11 Claims, 7 Drawing Sheets

U.S. PATENT DOCUMENTS

| | | |
|---|---|---|
| 6,000,787 A | 12/1999 | Weber et al. |
| 6,030,781 A | 2/2000 | Shieh |
| 6,043,080 A | 3/2000 | Lipshutz et al. |
| 6,048,691 A | 4/2000 | Maracas |
| 6,048,692 A | 4/2000 | Maracas et al. |
| 6,068,752 A | 5/2000 | Dubrow et al. |
| 6,080,295 A | 6/2000 | Parce et al. |
| 6,106,685 A | 8/2000 | McBride et al. |
| 6,107,044 A | 8/2000 | Nikiforov |
| 6,126,899 A * | 10/2000 | Woudenberg et al. .......... 422/50 |
| 6,156,181 A | 12/2000 | Parce et al. |
| 6,174,675 B1 | 1/2001 | Chow et al. |
| 6,197,595 B1 | 3/2001 | Anderson et al. |
| 6,210,986 B1 | 4/2001 | Arnold et al. |
| 6,235,471 B1 | 5/2001 | Knapp et al. |
| 6,238,624 B1 | 5/2001 | Heller et al. |
| 6,245,508 B1 | 6/2001 | Heller et al. |
| 6,258,606 B1 | 7/2001 | Kovacs |
| 6,271,021 B1 | 8/2001 | Burns et al. |
| 6,274,089 B1 | 8/2001 | Chow et al. |
| 6,280,590 B1 | 8/2001 | Cheng et al. |
| 6,306,590 B1 | 10/2001 | Mehta et al. |
| 6,315,940 B1 | 11/2001 | Nisch et al. |
| 6,316,201 B1 | 11/2001 | Nikiforov |
| 6,322,683 B1 | 11/2001 | Wolk et al. |
| 6,336,714 B1 | 1/2002 | Kawamura et al. |
| 6,342,142 B1 | 1/2002 | Ramsey |
| 6,379,974 B1 | 4/2002 | Parce et al. |
| 6,391,622 B1 | 5/2002 | Knapp et al. |
| 6,403,338 B1 | 6/2002 | Knapp et al. |
| 6,403,367 B1 | 6/2002 | Cheng et al. |
| 6,406,893 B1 | 6/2002 | Knapp et al. |
| 6,440,725 B1 * | 8/2002 | Pourahmadi et al. ...... 435/288.5 |
| 6,444,106 B1 | 9/2002 | Cherukuri et al. |
| 6,497,474 B2 * | 12/2002 | Irinoda et al. ................... 347/54 |
| 2001/0012612 A1 | 8/2001 | Petersen et al. |
| 2001/0020589 A1 | 9/2001 | Kopf-Sill |
| 2002/0008028 A1 | 1/2002 | Jacobson et al. |
| 2002/0008029 A1 | 1/2002 | Williams et al. |
| 2002/0008030 A1 | 1/2002 | Ramsey |
| 2002/0048768 A1 | 4/2002 | Nikiforov |
| 2002/0051971 A1 | 5/2002 | Stuelpnagel et al. |
| 2002/0055167 A1 | 5/2002 | Pourahmadi et al. |
| 2002/0070166 A1 | 6/2002 | Backhouse |
| 2002/0187560 A1 * | 12/2002 | Pezzuto et al. ................ 436/180 |
| 2003/0034740 A1 * | 2/2003 | Coll et al. ................ 315/111.21 |

* cited by examiner

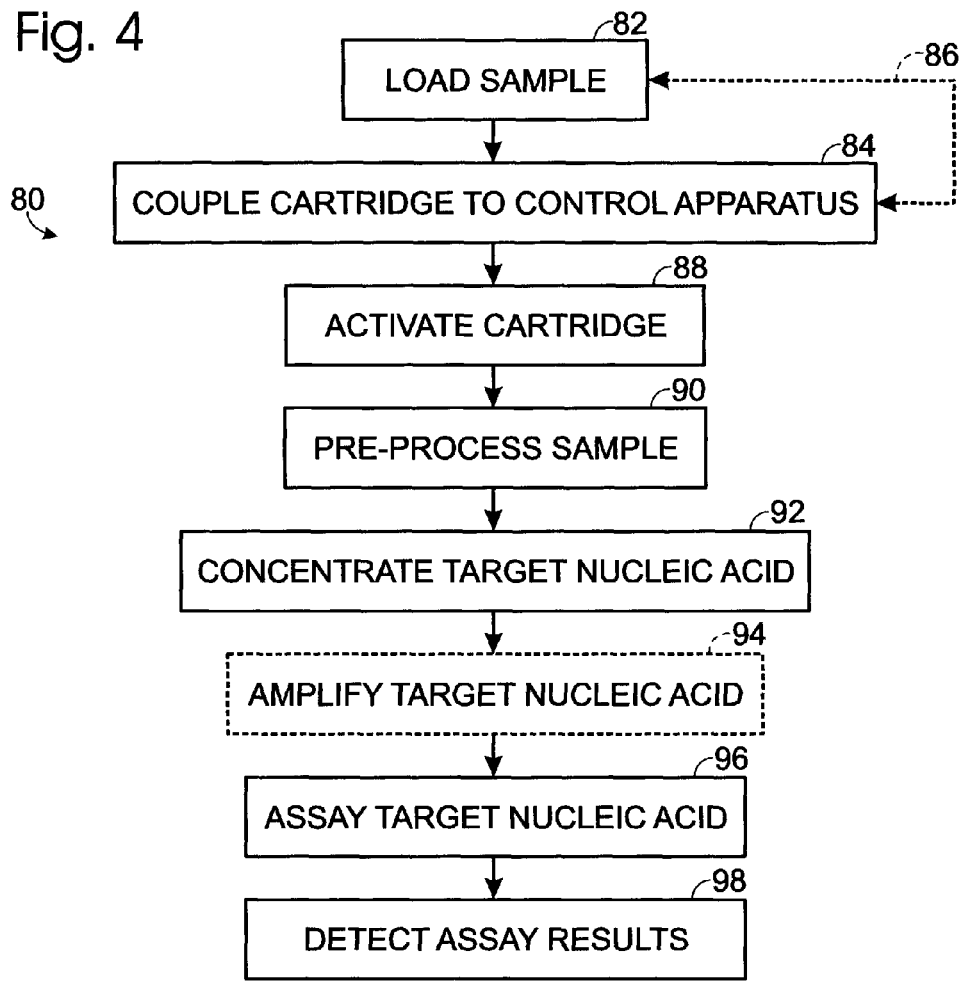
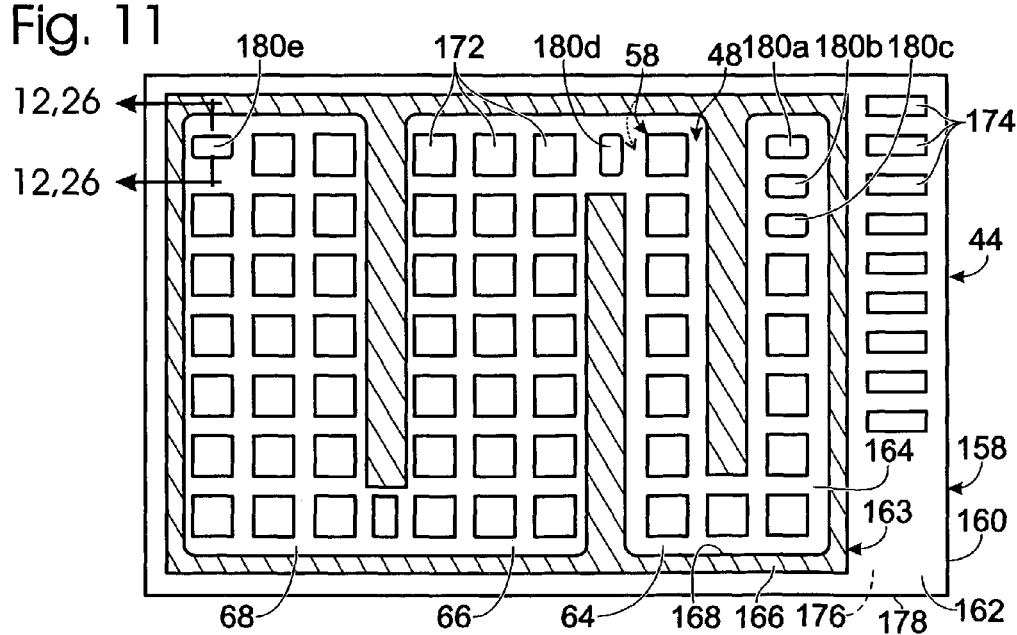

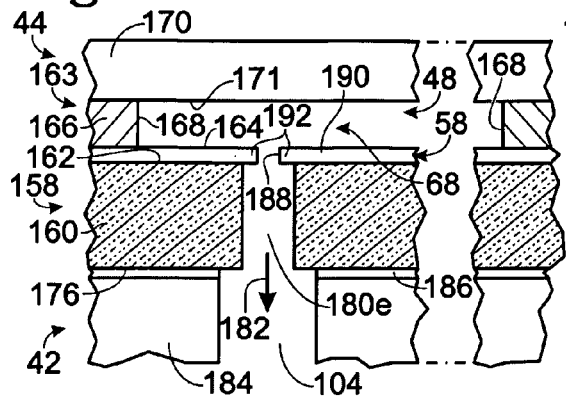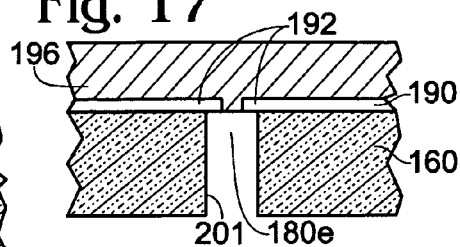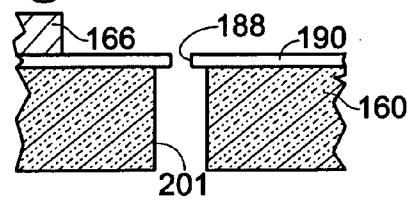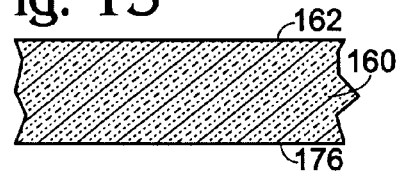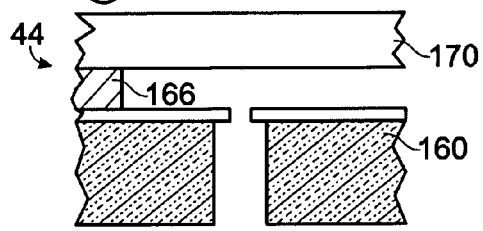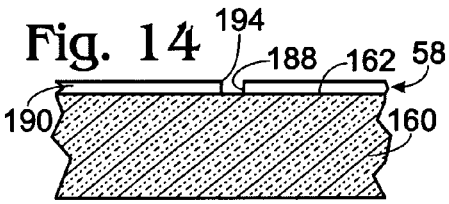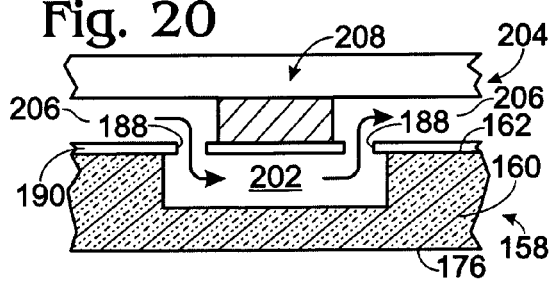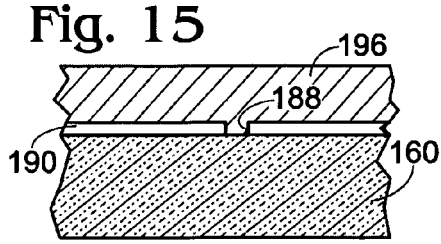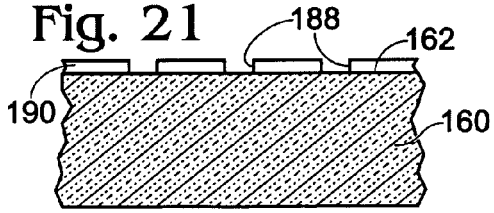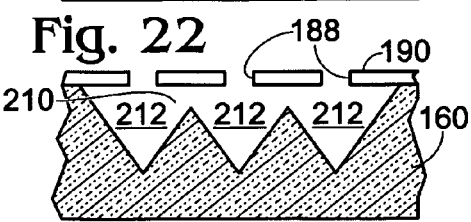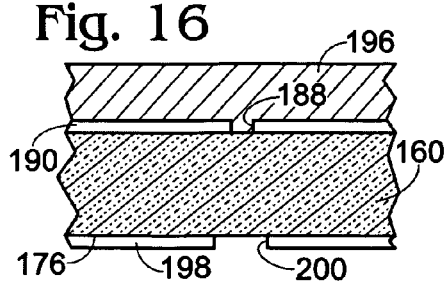

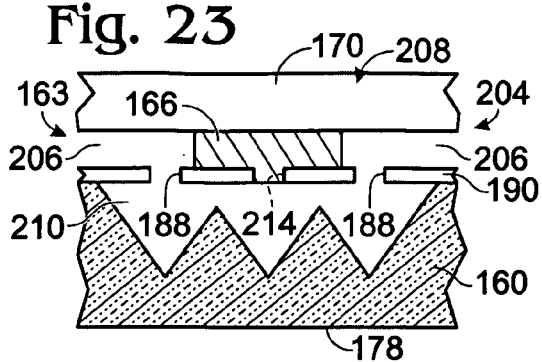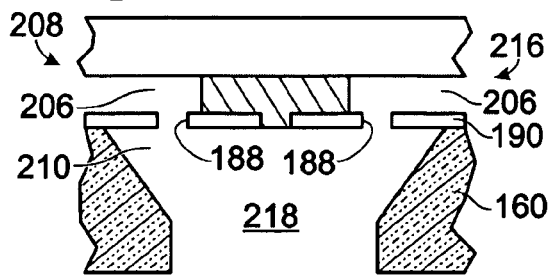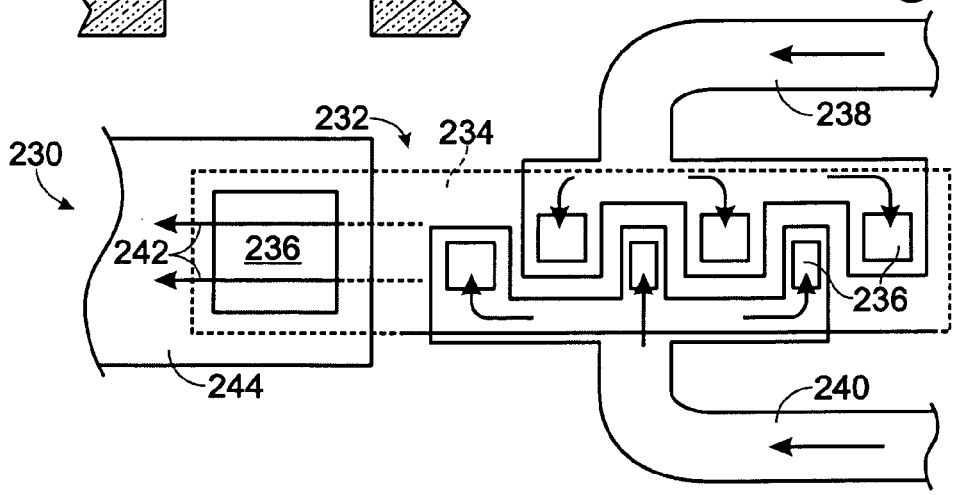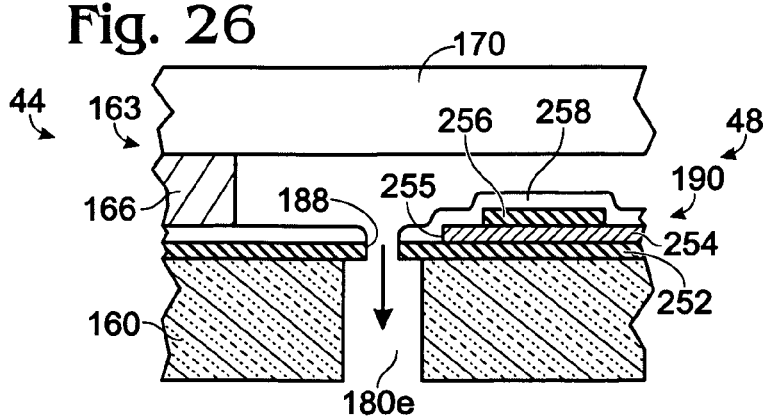

MICROFLUIDIC SYSTEM UTILIZING THIN-FILM LAYERS TO ROUTE FLUID

BACKGROUND

Rapid progress in genomics, proteomics, and cell analysis has pushed the biotechnology sector to develop faster and more efficient devices for analyzing biological samples. Accordingly, the biotechnology sector has directed substantial effort toward developing miniaturized microfluidic devices, often termed labs-on-a-chip, for sample manipulation and analysis. Such devices may analyze samples in small volumes of liquid, providing more economical use of reagents and sample, and in some cases dramatically speeding up assays. These devices offer the future possibility of human health assessment, genetic screening, and pathogen detection as routine, relatively low-cost procedures carried out very rapidly in a clinical setting or in the field. In addition, these devices have many other applications for manipulation and/or analysis of nonbiological samples.

Despite the sophistication of the electronics industry, microfluidic devices have not sufficiently integrated electronic circuitry into the combined electrical and fluidic manipulation of samples. For example, one class of microfluidic devices lacks the capability to electrically manipulate samples. This first class of devices may be inadequate for the control and monitoring of assay conditions in small volumes. Furthermore, devices of this first class may not be able to perform sample analyses of charged analytes, such as nucleic acids, on a time-scale afforded by electrical manipulation. A second class of microfluidic devices affords electrical, but not electronic, sample and fluid manipulation. This second class of devices may be capable of combined electrical and mechanical fluid/sample manipulation. However, without the capability of electronic switching, this second class cannot control a high density of electrical devices in the small area that is available proximate the fluid networks of such microfluidic devices. Accordingly, this second class also is limited in its ability to perform carefully regulated sample manipulations in small volumes. A third class of microfluidic devices includes integrated electronic circuitry to manipulate samples and fluids electronically. However, this third class of devices does not integrate the electronic circuitry effectively into the architecture of fluid flow paths within the devices.

SUMMARY OF THE INVENTION

Systems are provided, including apparatus and methods, for microfluidic processing and/or analysis of samples. The systems include a microfluidic device having a substrate and a thin-film layer formed on the substrate. The thin-film layer may be included in electronics formed on the substrate. The electronics may provide electronic devices configured to sense or modify a property of the sample. The thin-film layer defines an opening for routing fluid and/or sample within the device.

BRIEF DESCRIPTION OF THE DRAWINGS

FIG. 4 is a flowchart illustrating an exemplary method of operation of the cartridge and control apparatus of FIG. 1, in accordance with an embodiment of the invention.

FIG. 11 is a plan view of the assay portion included in the cartridge of FIGS. 1 and 5, viewed from external the cartridge and showing selected aspects of the assay portion, in accordance with an embodiment of the invention.

FIG. 12 is a fragmentary sectional view of the assay portion of FIG. 11, viewed generally along line 12-12 of FIG. 11, and shown attached to the fluid-handling portion of the cartridge of FIGS. 1 and 5, in accordance with an embodiment of the invention.

FIGS. 13-19 are fragmentary sectional views of a substrate during its modification to produce the assay portion shown in FIG. 12.

FIG. 20 is a schematic view of a channel that fluidly connects two fluid compartments formed adjacent a substrate surface, in which the channel enters and exits the substrate at the surface without communicating with the opposing surface of the substrate, in accordance with an embodiment of the invention.

FIGS. 21-23 are fragmentary sectional views of a substrate during its modification to produce the channel of FIG. 20.

FIG. 24 is a fragmentary sectional view of a modified version of the channel of FIG. 23.

FIG. 25 is a plan view of an embodiment of a mixing chamber that may be formed in an assay portion using a variation of the substrate modification illustrated in FIGS. 21-23.

FIG. 26 is a more detailed view of selected aspects of FIG. 12, illustrating disposition of selected film layers relative to an assay chamber and a substrate-defined channel, in accordance with an embodiment of the invention.

DETAILED DESCRIPTION

Systems, including apparatus and methods, are provided for microfluidic manipulation and/or analysis of samples. The systems include a microfluidic device having a thin-film layer formed on a substrate. The thin-film layer may perform a dual role in the device. In one role, the thin-film layer may form a portion of electronic circuitry formed on the substrate. The electronic circuitry may be configured to sense and/or modify a property of fluid and/or sample that enters a fluid compartment near the circuitry. Accordingly, the circuitry may include one or more electrodes, heaters, temperature sensors, and/or the like formed near a surface of the substrate. In a second role, the thin-film layer may define an opening that adjoins the fluid compartment. The opening defines an end region of a channel that extends into the substrate. The channel may fluidly connect fluid compartments on the same and/or opposing sides of the substrate. The opening may have a diameter that is less than the diameter of the channel within the substrate. Accordingly, because such openings may be dimensioned and positioned accurately, fluid flow may be routed with greater flexibility and precision based on fluid pathways defined during fabrication of the circuitry.

Further aspects are provided in the following sections: (I) microfluidic analysis with an integrated cartridge, (II) microfluidic systems, (III) samples, and (IV) assays.

I. Microfluidic Analysis with an Integrated Cartridge

This section describes a microfluidic system that includes an integrated microfluidic device, in the form of a cartridge, for processing and/or analysis of samples. This section also includes methods of using the device. Additional aspects of the cartridge and methods are described below in Section II. Furthermore, aspects of the cartridge and methods described below may be used on any of the samples described in Section III and/or using any of the assays described in Section IV.

Figure 1:
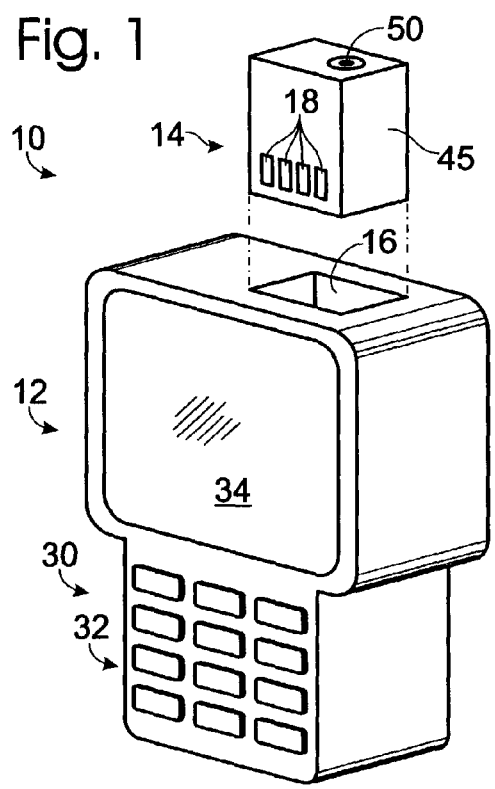
FIG. 1 is an isometric view of a microfluidic system having an integrated microfluidic cartridge aligned for mating with an exemplary control apparatus, the control apparatus being configured to power and control operation of the mated cartridge in sample processing and/or analysis, in accordance with an embodiment of the invention.
Figure 2:
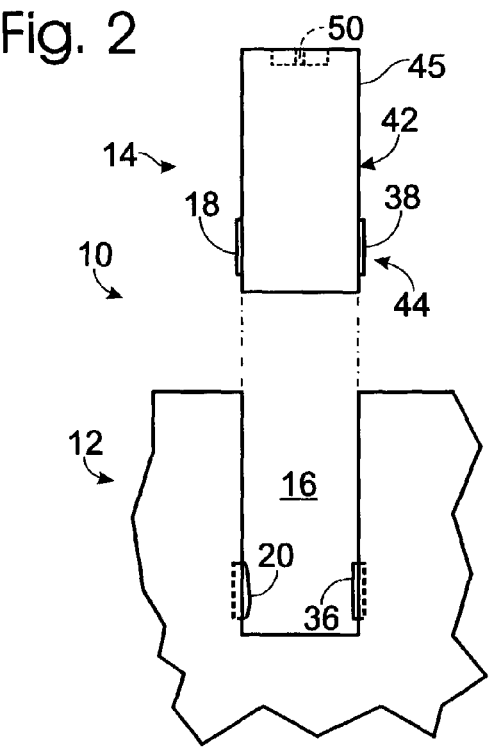
FIG. 2 is a fragmentary sectional view showing selected aspects of the cartridge and control apparatus of FIG. 1.
Figure 3:
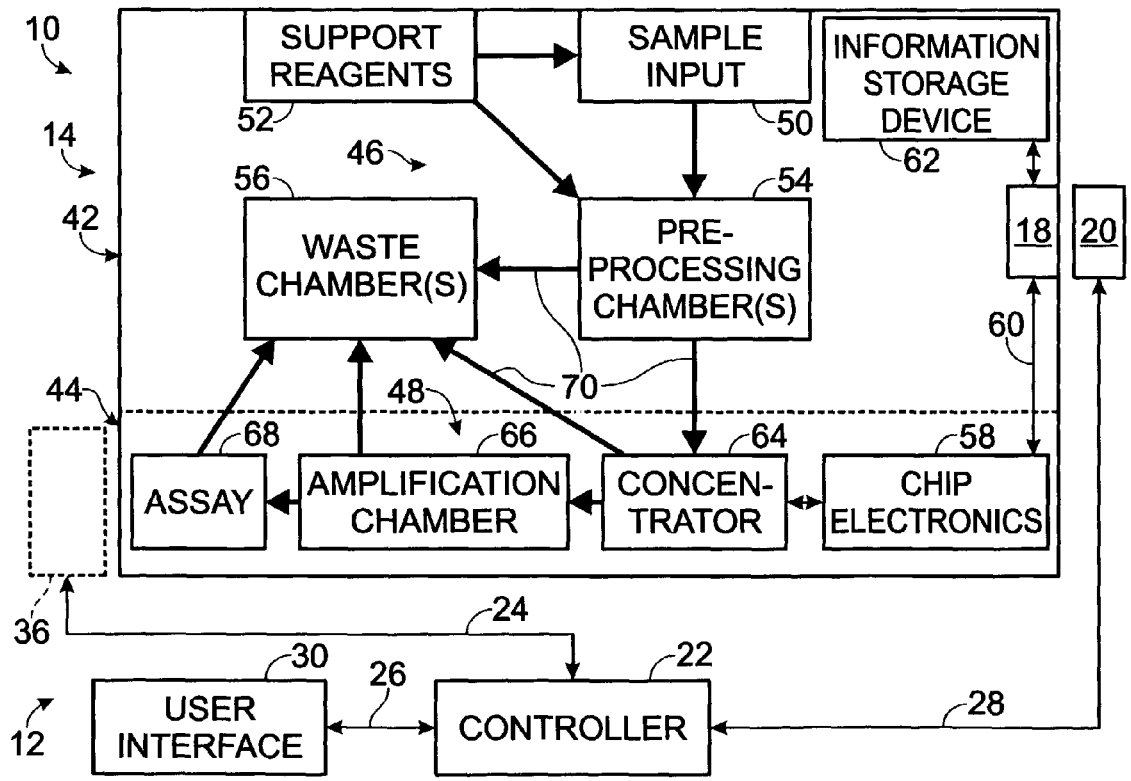
FIG. 3 is a schematic view of the cartridge and control apparatus of FIG. 1, illustrating movement of fluid, sample, electricity, digital information, and detected signals, in accordance with an embodiment of the invention.

FIGS. 1-3 show an embodiment of a microfluidic system 10 for processing and analysis of samples, particularly samples containing nucleic acids. FIGS. 1 and 2 show isometric and sectional views, respectively, of the system. FIG. 3 is a schematic representation of system 10, illustrating selected aspects of the system. System 10 includes a control apparatus 12 and an integrated cartridge 14 that is configured to be electrically coupled to control apparatus 12. In FIGS. 1 and 2, cartridge 14 is shown aligned and positioned to be received by, and thus installed in, the control apparatus. As used herein, the term "cartridge" describes a small modular unit designed to be installed in a larger control apparatus. As used herein, the term "installed in" indicates that the cartridge has been mated properly with the control apparatus, generally by at least partially inserting the cartridge in the control apparatus. Accordingly, control apparatus 12 may include a recess 16 that matingly receives cartridge 14, for example, by coupling through an electrical interface formed through contact between electrical contact pads 18 on cartridge 14 and corresponding contact structures 20 positioned in recess 16 (see FIG. 2). Alternatively, control apparatus 12 may interface electrically with cartridge 14 conductively, capacitively, and/or inductively using any other suitable structures. Control apparatus 12 may have any suitable size, for example, small enough to be held by hand, or larger for use on a bench-top or floor.

Control apparatus 12 is configured to send and receive control signals to cartridge 14, in order to control processing in cartridge 14. In some embodiments, cartridge 14 includes detection electronics. With such electronics, control apparatus receives signals from cartridge 14 that are utilized by control apparatus 12 to determine an assay result. The control apparatus may monitor and control conditions within the cartridge (such as temperature, flow rate, pressure, etc.), either through an electrical link with electronic devices within the cartridge and/or via sensors that interface with the cartridge. Alternatively, or in addition, control apparatus 12 may read information from an information storage device on the cartridge (see below) to ascertain information about the cartridge, such as reagents contained by the cartridge, assays performed by the cartridge, acceptable sample volume or type, and/or the like. Accordingly, control apparatus 12 generally provides some or all of the input and output lines described below in Section II, including power/ground lines, data input lines, fire pulse lines, data output lines, and/or clock lines, among others.

Control apparatus 12 may participate in final processing of assay data, or may transfer assay data to another device. Control apparatus 12 may interpret results, such as analysis of multiple data points (for example, from binding of a test nucleic acid to an array of receptors (see below)), and/or mathematical and/or statistical analysis of data. Alternatively, or in addition, control apparatus 12 may transfer assay data to another device, such as a centralized entity. Accordingly, control apparatus 12 may codify assay data prior to transfer.

Control apparatus 12 includes a controller 22 that processes digital information (see FIG. 3). The controller generally sends and receives electrical signals to coordinate electrical, mechanical, and/or optical activities performed by control apparatus 12 and cartridge 14, shown by double-headed arrows at 24, 26, 28.

Control apparatus 12 may communicate, shown at 26 in FIG. 3, with a user through a user interface 30. The user interface may include a keypad 32 (see FIG. 1), a screen 34, a keyboard, a touchpad, a mouse, and/or the like. The user interface typically allows the user to input and/or output data. Inputted data may be used, for example, to signal the beginning of sample processing, to halt sample processing, to input values for various processing parameters (such as times, temperatures, assays to be performed, etc.), and/or the like. Outputted data, such as stage of processing, cartridge parameters, measured results, etc. may be displayed on screen 34, sent to a printing device (not shown), stored in onboard memory, and/or sent to another digital device such as a personal computer, among others.

Control apparatus 12 also may include one or more optical, mechanical and/or fluid interfaces with cartridge 14 (see FIGS. 2 and 3). An optical interface 36 may send light to and/or receive light from cartridge 14. Optical interface 36 may be aligned with an optically transparent region 38 of cartridge 14 when the cartridge mates with control apparatus 12 (see FIG. 2 and discussion below). Accordingly, optical interface 36 may act as a detection mechanism having one or more emitters and detectors to receive optical information from the cartridge. Such optical information may relate to assay results produced by processing within the cartridge. Alternatively, or in addition, optical interface 36 may be involved in aspects of sample processing, for example, providing a light source for light-catalyzed chemical reaction, sample disruption, sample heating, etc. In any case, operation of optical interface 36 may be directed by controller 22, with corresponding measurements received by controller 22, as shown at 24 in FIG. 3, thus allowing measurements from optical interface 36 to be processed and stored electronically. Control apparatus 12 may include one or more electronically controlled mechanical interfaces (not shown), for example, to provide or regulate pressure on the cartridge. Exemplary mechanical interfaces of control apparatus 12 may include one or more valve actuators, valve regulators that control valve actuators, syringe pumps, sonicators, and/or pneumatic pressure sources, among others. In some embodiments, the control apparatus may include one or more fluid interfaces that fluidly connect the control apparatus to the cartridge. For example, the control apparatus may include fluid reservoirs that store fluid and deliver the fluid to the cartridge. However, control apparatus 12 shown here is not configured to couple fluidly to cartridge 14. Instead, in this embodiment, cartridge 14 is a closed or isolated fluid system during operation, that is, a fluid network in which fluid is not substantially added to, or removed from, the network after the sample is received. Further aspects of optical detection, and mechanical and fluid interfaces in microfluidic systems are described below in Section II.

Cartridge 14 may be configured and dimensioned as appropriate. In some embodiments, cartridge 14 is disposable, that is, intended for one-time use to analyze one sample or a set of samples (generally in parallel). Cartridge 14 may have a size dictated by assays to be performed, fluid volumes to be manipulated, nonfluid volume of the cartridge, and so on. However, cartridge 14 typically is small enough to be easily grasped and manipulated with one hand (or smaller).

Cartridge 14 typically includes at least two structurally and functionally distinct components: a fluid-handling portion 42 and an assay (or chip) portion 44. Fluid-handling portion may include a housing 45 that forms an outer mechanical interface with the control apparatus, for example, to operate valves and pumps. Housing may define the structure of interior fluid compartments. Housing 45 also substantially may define the external structure of the cartridge and thus may provide a gripping surface for handling by a user. Assay portion 44 may be attached fixedly to fluid-handling portion 42, for example, on an exterior or interior surface of fluid-handling portion 42. External attachment of assay portion 44 may be suitable, for example, when results are measured optically, such as with optical interface 36. Internal and/or external attachment may be suitable when results are measured electrically, or when fluid-handling portion 42 is optically transparent. Assay portion 44 also typically is connected fluidically to fluid-handling portion 42, as described below, to allow exchange of fluid between these two portions.

Fluid-handling portion 42 thus may be configured to receive fluids from external the cartridge, store the fluids, and deliver the fluids to fluid compartments in both fluid-handling portion 42 and assay portion 44, for example, by mechanically driven fluid flow. Accordingly, fluid-handling portion may define a fluid network 46 with a fluid capacity (volume) that is substantially larger than a corresponding fluid network (or fluid space) 48 of assay portion 44. Each fluid network may have one fluid compartment, or more typically, plural fluidically connected fluid compartments, generally chambers connected by fluid conduits.

Fluid-handling portion 42 includes a sample input site or port 50. Sample input site 50 is generally externally accessible but may be sealable after sample is introduced to the site. Cartridge 14 is shown to include one sample input site 50, but any suitable number of sample input sites may be included in fluid-handling portion 42.

Fluid-handling portion 42 also includes one or more reagent reservoirs (or fluid storage chambers) 52 to carry support reagents (see FIG. 3). Reagent reservoirs 52 each may be externally accessible, to allow reagent loading after the fluid-handling portion has been manufactured. Alternatively, some or all of reagent reservoirs 52 may be loaded with reagent during manufacturing. Support reagents generally include any fluid solution or mixture involved in sample processing, analysis, and/or general operation of cartridge 14.

Fluid-handling portion 42 also may include one or more additional chambers, such as a pre-processing chamber(s) 54 and/or a waste chamber(s) 56. Pre-processing chamber(s) 54 and waste chamber(s) 56 may be accessible only internally, for example, through sample input site 50 and/or reagent reservoirs 52, or one or more may be externally accessible to a user. Pre-processing chamber(s) are fluid passages configured to modify the composition of a sample, generally in cooperation with fluid flow. For example, such passages may isolate analytes (such as nucleic acids) from inputted sample, that is, at least partially separating analyte from waste material or a waste portion of the sample, as described below. Further aspects of fluid-handling portions are described below in Section II.

In a preferred embodiment, the fluid-handling portion 42 and in fact all fluid compartments of cartridge 14 are sealed against customer access, except for the sample input 50. This sealing may operate to avoid potential contamination of reagents, to assure safety, and/or to avoid loss of fluids from fluid-handling portion 42. Some of the reagents and/or processing byproducts resultant from pre-processing and/or additional processing may be toxic or otherwise hazardous to the user if the reagents or byproducts leak out and/or come in contact with the user. Furthermore, some of the reagents may be very expensive and hence in minimal supply in cartridge 14. Thus, the preferred implementation of cartridge 14 is an integral, sealed, disposable cartridge with a fluid interface(s) only for sample input 50, an electrical interface 18, and optional mechanical, optical and/or acoustic interfaces.

Assay portion 44 is configured for further processing of nucleic acid in fluid network 48 after nucleic acid isolation in fluid-handling portion 42. Accordingly, assay portion 44 relies on electronics or electronic circuitry 58, which may include thin-film electronic devices to facilitate controlled processing of nucleic acids received from fluid-handling portion 42. By contrast, bulk fluid flow in assay portion 44 may be mediated by mechanically driven flow of fluid from fluid-handling portion 42, through assay portion 44, and back to portion 42.

Electronic circuitry 58 of the assay portion may include thin-film electronic devices to modify and/or sense fluid and/or analyte properties. Exemplary roles of such thin-film devices may include concentrating the isolated nucleic acids, moving the nucleic acids to different reaction chambers and/or assay sites, controlling reaction conditions (such as during amplification, hybridization to receptors, denaturation of double-stranded nucleic acids, etc.), and/or the like (see Section II also). The thin-film devices may be operably coupled to any regions of fluid network 48. Operably coupled may include direct contact with fluid, for example, with electrodes, or spaced from fluid by one or more insulating thin-film layers (see below). In either case, the operably disposed devices may be disposed near the surface of the substrate (see below). Further aspects of the electronic circuitry, thin-film layers, and substrates are described below in this section and in Section II.

Electronic circuitry 58 of assay portion 44 is controlled, at least in part, by electrically coupling to control apparatus 12. For example, as shown in FIG. 3, controller 22 may be coupled, shown at 28, via contact structures 20, with contact pads 18 disposed on fluid-handling portion 42 of cartridge 14. In turn, contact pads 18 may be electrically coupled with electronic circuitry 58, as shown at 60. One or more additional integrated circuits, or interface circuits, may be coupled electrically to contact pads 18 intermediate to circuitry 58, for example, to allow circuitry 58 to have greater complexity and/or to minimize the number of distinct contact pads (or sites) on cartridge 14. Thus, the contact pads alone or in combination with the interface circuits form an interconnect circuit that electrically couples the electronics to the controller when the cartridge is installed in the control apparatus. Contact pads also may couple to an electronic information storage device 62 carried in cartridge 14, for example, in fluid-handling portion 42, as shown. The information storage device may store information that relates to the cartridge, such as fluid network configurations, reservoir contents, assay capabilities, assay parameters, and/or the like. In alternative embodiments, contact pads 18 or other electrical coupling structures may be disposed on assay portion 44 instead of, or in addition to, being included in fluid-handling portion 42.

Assay portion 44 typically is configured to carry out nucleic acid processing in fluid network 48, at least partially by operation of circuitry 58. Here, fluid network 48 is shown to include three functional regions: a concentrator 64, an amplification chamber 66, and an assay chamber 68. As described in more detail below, each of these functional regions may include electrodes to facilitate nucleic acid retention and release (and thus concentration), and/or directed movement toward a subset of the electrodes. Concentrator 64 and chambers 66, 68 may be defined by distinct compartments/passages, for example, as a serial array of compartments, as shown. Alternatively, these functional regions may be partially or completely overlapping, for example, with all provided by one chamber.

Concentrator 64 is configured to concentrate nucleic acids received from pre-processing chamber 54. Electrodes of concentrator 64 may be electrically biased positively, while allowing fluid to pass from fluid-handling portion 42, through the concentrator, and back to waste chamber 56 in fluid-handling portion 42. Accordingly, concentrator 64 may be connected fluidically to fluid-handling portion 42 at plural discrete sites (see FIGS. 5-11), allowing the concentrator to serve as a conduit. The conduit may allow transfer of a fluid volume (between two fluid-handling portion reservoirs) that is substantially larger than the fluid capacity of the concentrator. This processing step removes fluid, and may partially purify the nucleic acids by removing material that is positively charged, uncharged, or weakly negatively charged, among others.

Amplification chamber 66 may be used to copy one or more target nucleic acid (or nucleic acids) from among the concentrated nucleic acids, using an amplification reaction to increase assay sensitivity. An amplification reaction generally includes any reaction that increases the total number of molecules of a target nucleic acid (or a region contained within the target species), generally resulting in enrichment of the target nucleic acid relative to total nucleic acids. Enzymes that replicate DNA, transcribe RNA from DNA, and/or perform template-directed ligation of primers, may mediate the amplification reaction. Dependent upon the method and the enzymes used, amplification may involve thermal cycling (for example, polymerase chain reaction (PCR) or ligase chain reaction (LCR)) or may be isothermal (for example, strand-displacement amplification (SDA) or nucleic acid sequence-based amplification (NASBA)). With any of these methods, temperature control in chamber 66 may be determined by heaters, such as thin-film heaters included in circuitry 58. Nucleic acids may be labeled during amplification to facilitate detection, for example, by incorporation of labeled primers or nucleotides. Primers or nucleotides may be labeled with dyes, radioisotopes, or specific binding members, as described below in Section II and listed in Table 1. Alternatively, nucleic acids may be labeled in a separate processing step (for example, by terminal transferase, primer extension, affinity reagents, nucleic acid dyes, etc.), or prior to inputting the sample. Such separate labeling may be suitable, for example, when the amplification step is omitted because a sufficient amount of the target nucleic acid is included in the inputted sample.

Assay chamber 68 may perform a processing step that separates or distinguishes nucleic acids according to specific sequence, length, and/or presence of sequence motifs. In some embodiments, the assay chamber includes one or plural specific receptors for nucleic acids. Receptors may include any agent that specifically binds target nucleic acids. Exemplary receptors may include single-stranded nucleic acids, peptide nucleic acids, antibodies, chemical compounds, polymers, etc. The receptors may be disposed in an array, generally immobilized at defined positions, so that binding of a target nucleic acid to one of the receptors produces a detectable signal at a defined position(s) in the assay chamber. Accordingly, when amplification is used, amplified nucleic acids (targets) contact each of the receptors to test binding. A receptor array may be disposed proximate to electrodes that concentrate the targets electrically over receptors of the array, as described further below. In alternative embodiments, the assay chamber may separate target nucleic acids according to size, for example, using electrophoresis and/or chromatography. Alternatively, or in addition, the assay chamber may provide receptors that are not immobilized, such as molecular beacon probes and/or may provide a site for detection without receptors.

Optical interface 36 may measure sample processing at any suitable position of assay portion 44. For example, optical interface may include separate emitter-detector pairs for monitoring amplification of nucleic acids in amplification chamber 66, and for detecting binding and/or position of amplified nucleic acids after processing in assay chamber 68, as described above. Alternatively, or in addition, the optical interface may monitor fluid movement through chip fluid network 48.

FIG. 3 shows exemplary directions of fluid movement (reagents and/or sample) through fluid networks 46 and 48 during sample processing, indicated by thickened arrows, as shown at 70. Generally, fluid flows from reagent reservoirs 52 through sample input site 50 and pre-processing chamber(s) 54 to waste chamber(s) 56 and assay portion 44 (see below). Fluid that enters assay portion 44 from fluid-handling portion 42 may flow back to waste chamber(s) 56 or may be moved to other fluid compartments in the assay portion.

FIG. 4 shows a flowchart illustrating an exemplary method 80 for operation of cartridge 14 with control apparatus 12 to analyze target nucleic acid(s) in a sample. First, sample may be introduced (loaded) at sample input site 50 of cartridge 14, for example, by injection, as shown at 82. Next, the cartridge with its sample may be electrically coupled to control apparatus 14, as shown at 84, for example, by mating the cartridge with recess 16 for conductive contact. As indicated at 86, such loading and coupling may be performed in reverse order, that is, the sample may be introduced into the cartridge after it has been coupled to the control apparatus. The cartridge then may be activated to initiate processing, as shown at 88. The cartridge may be activated by input from a user through user interface 30, by coupling the cartridge to the control apparatus, by introducing a sample, and/or the like. After activation, the sample is pre-processed, as shown at 90. Pre-processing typically moves the sample to pre-processing chamber 54, and treats the sample to release and isolate nucleic acids, when necessary, as described further below. The isolated nucleic acids are moved to concentrator 64 in assay portion 44, generally by mechanically driven flow, and concentrated, as shown at 92. The concentrated nucleic acids may be amplified selectively, if needed, as shown at 94, with use of primers targeted to nucleic acids of interest. Next, the amplified nucleic acids may be assayed, for example, by contacting a receptor or receptor array with the amplified nucleic acids, as shown at 96. Assay results then may be detected optically and/or electrically, as shown at 98.

Figure 5:
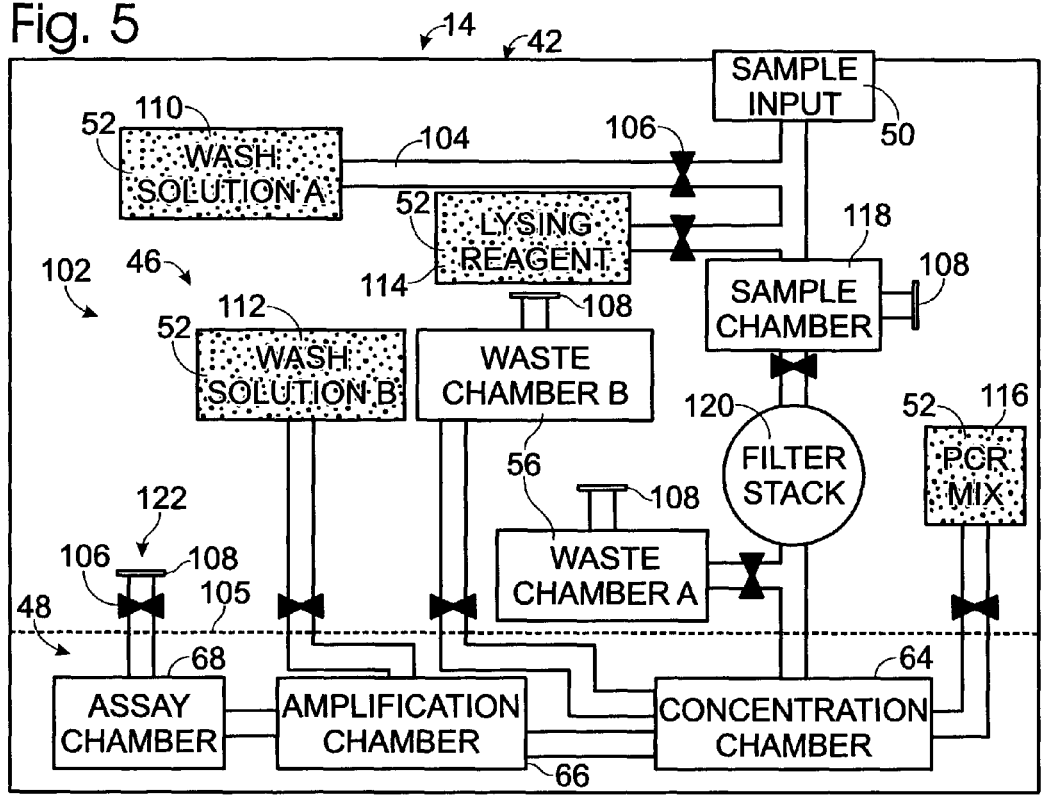
FIG. 5 is a more detailed schematic view of the cartridge of FIGS. 1 and 3, illustrating a fluid network for carrying out the method of FIG. 4.

FIG. 5 shows a more detailed representation of an exemplary self-contained fluid network 102 formed by interconnected fluid networks 46, 48 in fluid-handling portion 42 and assay portion 44 of cartridge 14, respectively. Chambers are represented as rectangles, or by a circle. Channels 104 that interconnect the chambers are represented by parallel lines. As shown, channels 104 fluidly connect fluid-handling portion 42 with assay portion 44 at positions where the channels cross an interface 105 between the two portions. Valves 106 are represented by solid "bowties" (closed valves) or by unfilled bowties (open valves; see below). Valves typically are electrically activated, and thus may be electrically coupled (not shown) to control apparatus 12. Alternatively, or in addition, valves may be mechanically operated by electrically activated valve actuators/regulators on control apparatus 12. Exemplary valves include solenoid valves and single use valves. Gas-selective vents 108 are represented by thin rectangles on terminated channels (see the vent on assay chamber 68, for example). Suitable valves and vents are described further in Section II.

FIG. 5 shows the cartridge ready to receive a sample and to be activated. Accordingly, the cartridge has been preloaded with reagents in reagent reservoirs 52, as shown by stippling to represent fluid. Preloaded reagent reservoirs 52 may carry wash solutions 110, 112 of suitable pH, buffering capacity, ionic strength, solvent composition, etc. One or more reservoirs 52 also may carry a lysing reagent 114, which may include, for example, a chaotropic agent, a buffer of high or low ionic strength, one or more ionic or nonionic detergents, an organic solvent(s), and/or the like. Furthermore, one or more reservoirs 52 may include an amplification mix, such as PCR mix 116, or any other mixture that includes one or more amplification reagents. In general, any nucleic acid(s) that selectively hybridizes to the nucleic acid(s) of interest may be an amplification reagent.

PCR mix 116 generally includes a suitable buffer, $Mg^{+2}$, specific primers for selective amplification of target nucleic acid(s), dNTPs, a heat stable polymerase, and/or the like. One or more primers and/or dNTPs may be labeled, for example with a dye or biotin, as described above. PCR mix 116 may be replaced with any other suitable amplification mixture, based on the amplification method implemented by the cartridge. Furthermore, in order to analyze RNA, PCR mix may include a reverse transcriptase enzyme. Alternatively, a separate reservoir may provide reagents to carry out synthesis of complementary DNA using the RNA as a template, generally prior to amplification.

Reagent reservoirs 52 may be configured to deliver fluid based on mechanically driven fluid flow. For example, reagent reservoirs 52 may be structured as collapsible bags, with a spring or other resilient structure exerting a positive pressure on each bag. Alternatively, reagent reservoirs 52 may be pressurized with a gas. Whatever the mechanism of pressurization, valve 106 may be operated to selectively control delivery of reagent from each reservoir. Section II describes additional exemplary mechanisms to produce mechanically driven fluid flow.

Cartridge 14 includes internal chambers for carrying out various functions. Internal chambers include waste chambers 56, in this case, two waste chambers, designated A and B. Waste chambers 56 receive fluids from reagent reservoirs 52 (and from sample input 50) and thus may include vents 108 to allow gas to be vented from the waste chambers. Internal chambers (passages) may include a sample chamber 118, a filter stack 120, and chip chambers 64, 66, 68. Sample chamber 118 and filter stack 120 are configured to receive and pre-process the sample, respectively, as described further below. Assay chamber 68 may be vented by a regulated vent 122, that is, a valve 106 that controls a vent 108. Some or all of the internal chambers and/or channels 104 may be primed with suitable fluid, for example, as part of cartridge manufacture. In particular, chambers/channels of assay portion 44 may be primed. Correspondingly, some chambers and/or channels may be unprimed prior to cartridge activation.

Figure 6:
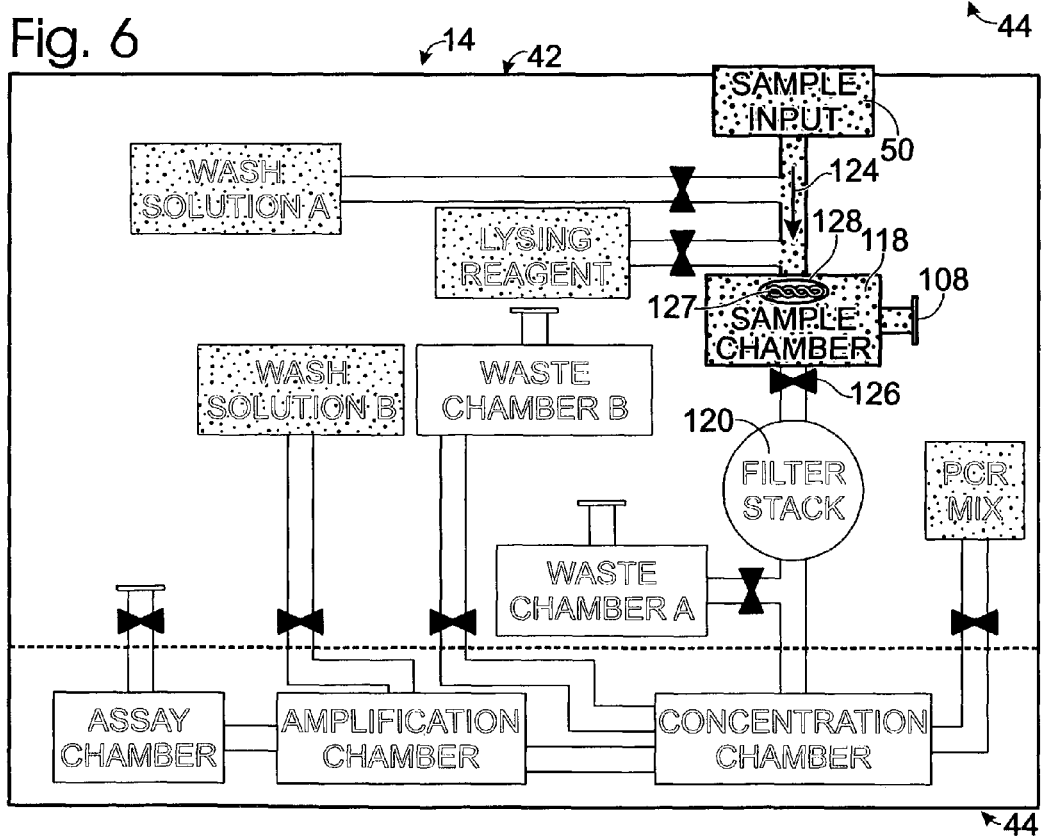
FIG. 6 is a schematic view emphasizing active regions of the cartridge of FIG. 5 during sample loading.

FIG. 6 shows active regions of fluid movement in cartridge 14 during sample loading. Here, and in FIGS. 7-10, heavy stippling indicates active regions, whereas light stippling indicates reagents or waste in reservoirs elsewhere in the cartridge. A sample, such as a liquid-based sample, is loaded at sample input site 50 and received by sample chamber 118, generally following a path indicated at 124. The volume of sample that may be loaded is limited here by a vent 108 on sample chamber 118, and by the capacity of sample chamber 118. Once sample chamber 118 is filled, vent 108 may provide a back pressure that limits introduction of additional sample. Alternatively, or in addition, an electrical or optical fluid sensor (not shown) may be placed within or around sample chamber 118 to signal when sample capacity is reached. A valve 126 downstream from sample chamber 118 may prevent the sample from flowing to filter stack 120 at this time, or the sample may be loaded directly onto the filter stack from sample input site 50, for example, by venting through waste chamber A.

The sample may be in any suitable form, for example, any of the samples described above in Section III. However, the cartridge embodiment described here is configured to analyze nucleic acids 127, so samples generally contain nucleic acids, that is, DNA and/or RNA, or be suspected of carrying nucleic acid. Nucleic acids 127 may be carried in tissue or biological particles, may be in an extract from such, and/or may be partially or fully purified. Cells 128, viruses, and cell organelles are exemplary biological particles. The loaded sample volume may be any suitable volume, based on sample availability, ease of handling small volumes, target nucleic acid abundance in the sample, and/or cartridge capacity, etc.

Figure 7:
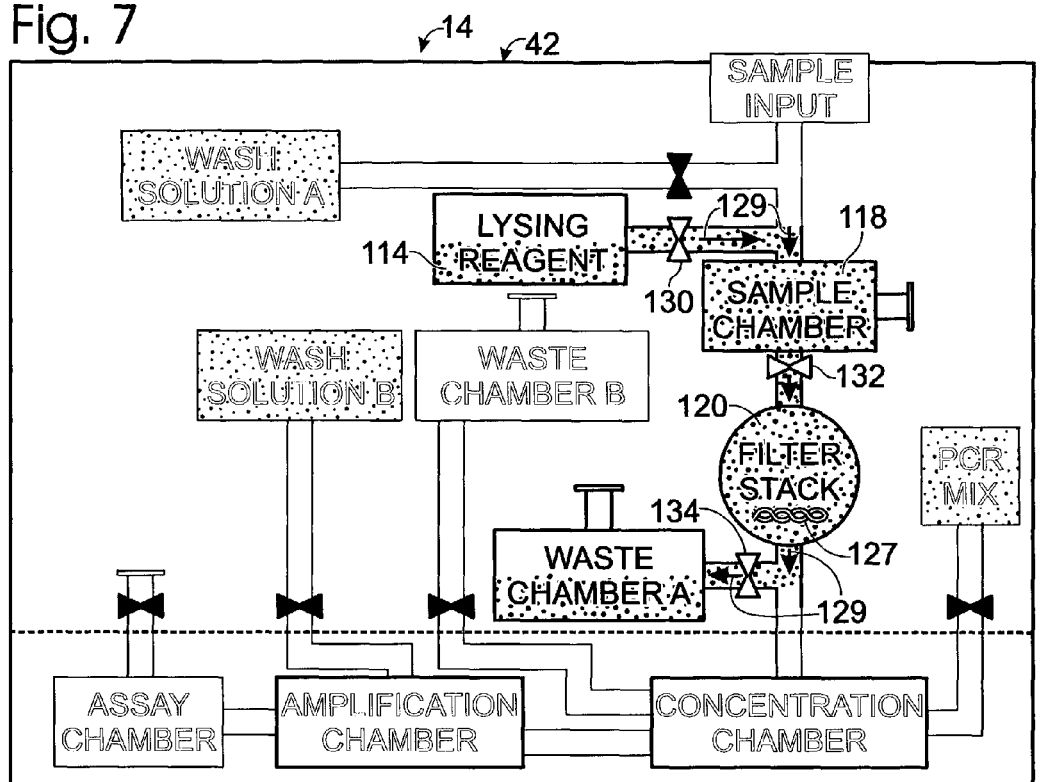
FIG. 7 is a schematic view emphasizing active regions of the cartridge of FIG. 5 during sample processing to isolate nucleic acids on a filter stack.

FIG. 7 shows active regions of fluid movement in cartridge 14 during sample pre-processing. Lysing reagent 114 may be introduced along path 129 by opening valves 130, 132, 134. The lysing reagent thus typically carries the sample with its nucleic acids 127 from sample chamber 118 to filter stack 120. Excess fluid may be carried to waste chamber A. The filter stack generally may be configured to perform nucleic acid isolation, that is, at least partial separation from sample waste material, through any or all of at least three functions: particle filtration, nucleic acid release from the sample, and retention of released nucleic acid. Waste material is defined here as any sample-derived component, complex, aggregate or particulate, among others, that does not correspond to the nucleic acid of interest. Exemplary waste material may include cell or viral debris, unbroken cells or virus particles, cell membranes, cytoplasmic components, soluble non-nucleic acid materials, insoluble non-nucleic acid materials, nucleic acids that are not of interest, and/or the like. Waste material also may be sample-derived fluid, removal of which concentrates the nucleic acids.

Filtration is any size selection process carried out by filters that mechanically retain cells, particles, debris and/or the like. Accordingly, the filter stack may localize sample particles (cells, viruses, etc.) for disrupting treatment and also may remove particulates that might interfere with downstream processing and/or fluid flow in cartridge fluid network 102. Suitable filters for this first function may include small-pore membranes, fiber filters, narrowed channels, and/or so on. One or more filters may be included in the filter stack. In some embodiments, the filter stack includes a series of filters with a decreasing exclusion limit within the series along the direction of fluid flow. Such a serial arrangement may reduce the rate at which filters become clogged with particles.

The sample retained on filter stack 120 may be subjected to a treatment that releases nucleic acids 127 from an unprocessed and/or less accessible form in the sample. Alternatively, or in addition, the releasing treatment may be carried out prior to sample retention on the filter stack. The treatment may alter the integrity of cell surface, nuclear, and/or mitochondrial membranes and/or may disaggregate subcellular structures, among others. Exemplary releasing treatments may include changes in pressure (for example, sonic or ultrasonic waves/ pulses or a pressure drop produced by channel narrowing as in a French press); temperature shift (heating and/or cooling); electrical treatment, such as voltage pulses; chemical treatments, such as with detergent, chaotropic agents, organic solvents, high or low salt, etc.; projections within a fluid compartment (such as spikes or sharp edges); and/or the like. Here, nucleic acids 127 are shown after being freed from cells 128 that carried the nucleic acids.

Nucleic acid retention is generally implemented downstream of the filters. Nucleic acid retention may be implemented by a retention matrix that binds nucleic acids 127 reversibly. Suitable retention matrices for this second function may include beads, particles, and/or membranes, among others. Exemplary retention matrices may include positively charged resins (ion exchange resins), activated silica, and/or the like. Once nucleic acids 127 are retained, additional lysing reagent or a wash solution may be moved past the retained nucleic acid 127 to wash away unretained contaminants.

Figure 8:
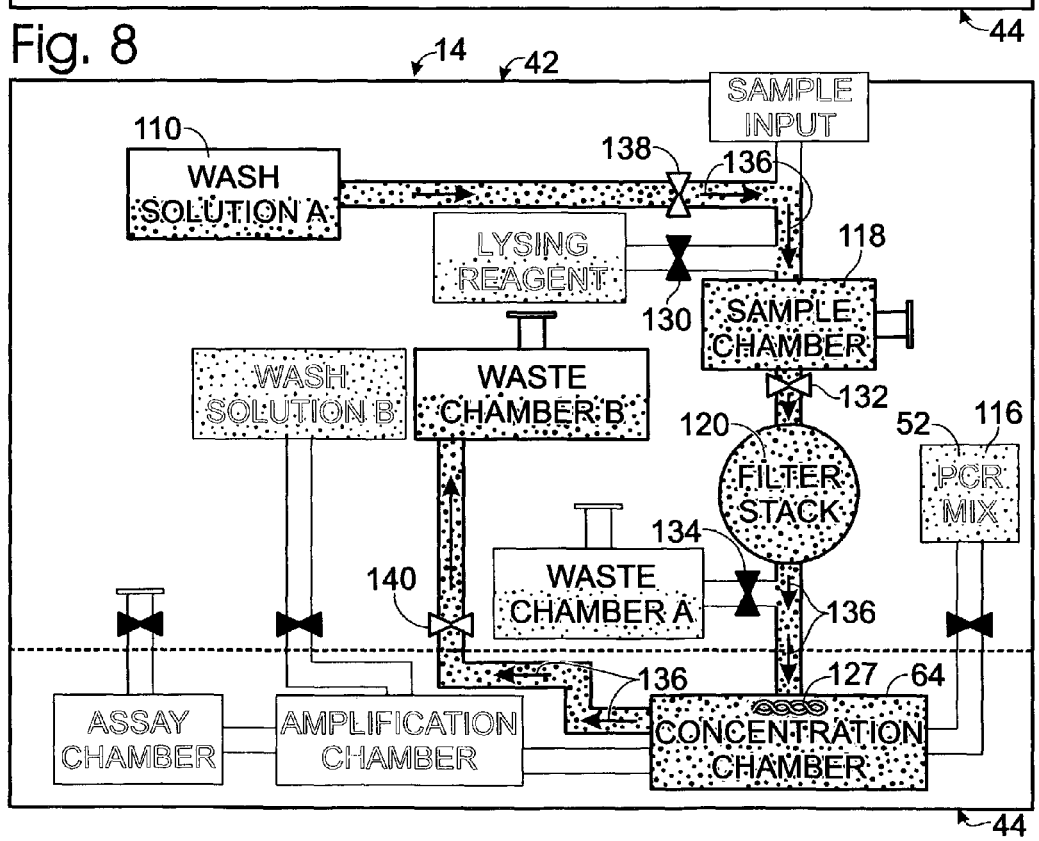
FIG. 8 is a schematic view emphasizing active regions of the cartridge of FIG. 5 during release of the nucleic acids from the filter stack and electrically determined concentration of the released nucleic acids on an assay portion of the cartridge.

FIG. 8 shows active regions of fluid movement in cartridge 14 during release of nucleic acids 127 from filter stack 120 and concentration of the released nucleic acids 127 in concentration chamber 64 of assay portion 44. Fluid flows from wash solution A, shown at 110, to a distinct waste chamber, waste chamber B, along fluid path 136, through sample chamber 118 and filter stack 120. To initiate flow along path 136, valves 130 and 134 are closed, valve 132 remains open, and valves 138 and 140 are opened. Wash solution A may be configured to release nucleic acids 127 that were retained in filter stack 120 (see FIG. 7). Accordingly, wash solution A may be formulated based on the mechanism by which nucleic acids 127 are retained by the retention matrix in the filter stack. Wash solutions to release retained nucleic acid may alter the pH, ionic strength, and/or dielectric constant of the fluid, among others. Exemplary wash solutions may include a high or low pH, a high or low ionic strength, an organic solvent, and/or so on. Pre-processing may provide a first-step concentration and purification of nucleic acids from the sample.

Released nucleic acids 127 may be concentrated (and purified) further at concentration chamber 64. Concentration chamber 64 typically is formed in assay portion 44, and includes one, or typically plural electrodes. At least one of the electrodes may be electrically biased (positively) before or as the released nucleic acids enter concentration chamber 64. As a result, nucleic acids 127 that flow through concentration chamber 64 may be attracted to, and retained by, the positively biased electrode(s). Bulk fluid that carries nucleic acids 127, and additional wash solution A, may be carried on to waste chamber B. Accordingly, nucleic acids 127 may be concentrated, and may be purified further by retention in concentration chamber 64. This concentration of nucleic acids 127 may allow assay portion 44 to have fluid compartments that are very small in volume, for example, compartments, in which processing occurs, having a fluid capacity of less than about one microliter. Further aspects of electrode structure, number, disposition, and coating are described below.

Figure 9:
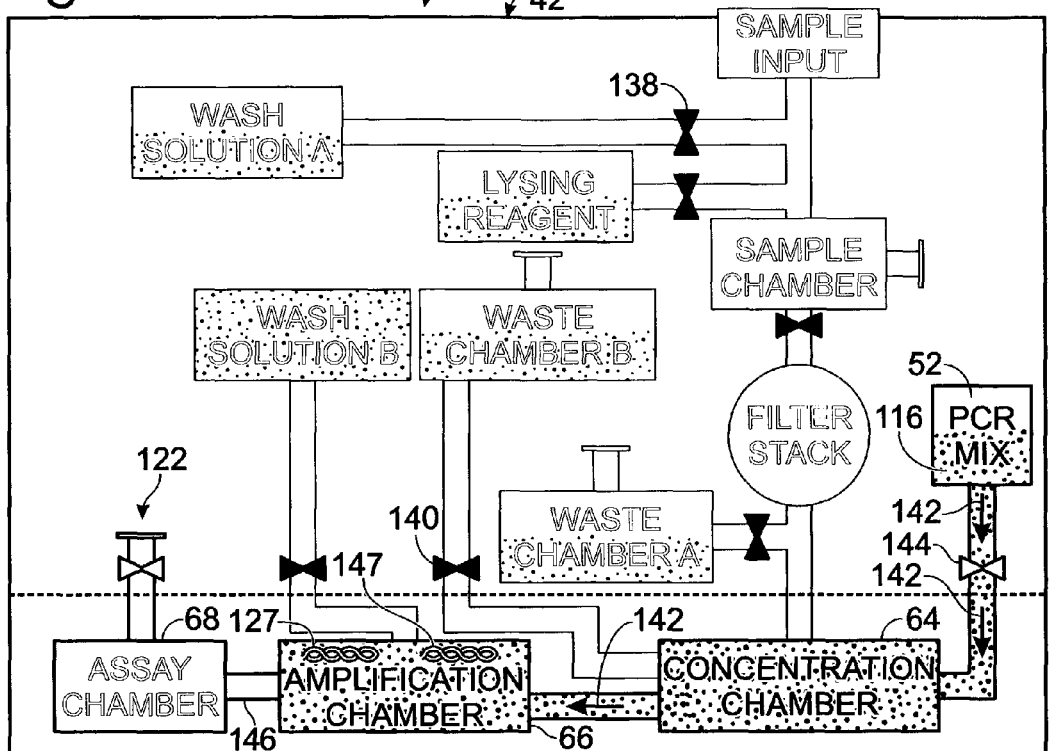
FIG. 9 is a schematic view emphasizing active regions of the cartridge of FIG. 5 during equilibration of the concentrated nucleic acids with amplification reagents and transfer to an amplification chamber on the assay portion.

FIG. 9 shows active regions of fluid movement in cartridge 14 during transfer of concentrated nucleic acids to amplification chamber 66 of assay portion 44. As shown, typically fluid flows from a chamber 52, holding PCR mix 116, to amplification chamber 66 along fluid path 142. To activate flow along path 142, valve 138 and 140 are closed, and valve 144 and vent-valve 122 are opened, as the retaining positive bias is removed from the electrode(s) in concentration chamber 64. PCR mix 116 may carry nucleic acids 127 by fluid flow. Alternatively, a positive bias may be imparted to electrodes in amplification chamber 66 (see below) to electrophoretically transfer nucleic acids 127 to amplification chamber 66, which is preloaded with PCR mix 116. In either case, flow of excess fluid out of amplification chamber 66 and into assay chamber 68 may be restricted, for example, by an electrical or optical sensor (not shown) that monitors fluid level in connecting channel 146 and signals timely closing of vent-valve 122. In some embodiments, concentration chamber 64 first may be equilibrated with PCR mix 116 prior to moving nucleic acids 127 to amplification chamber 66. For example, PCR mix 116 may be directed through an opened valve 140 to waste chamber B, before removing the retaining positive bias in concentration chamber 64 and opening vent-valve 122. Nucleic acids 127 positioned in amplification chamber 66 may be amplified, for example, by isothermal incubation or thermal cycling, to selectively increase the amount of nucleic-acid targets (or target regions) of interest 147 among nucleic acids 127, or, in some cases, may remain unamplified.

Figure 10:
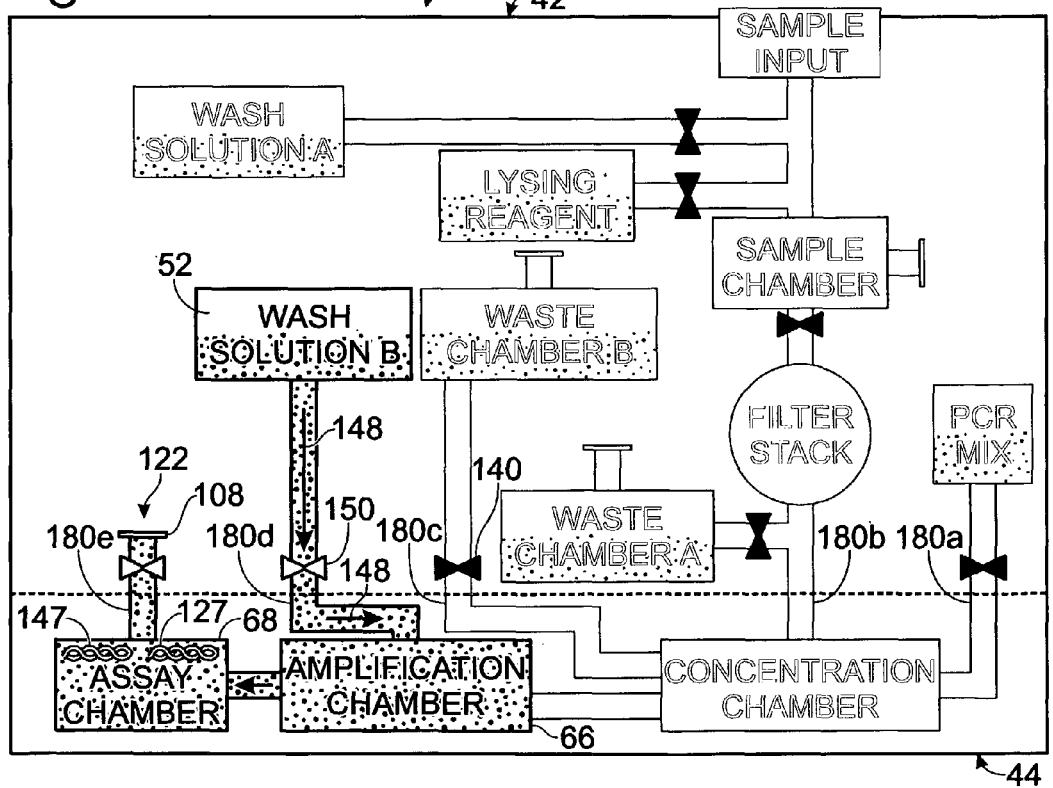
FIG. 10 is a schematic view emphasizing active regions of the cartridge of FIG. 5 during transfer of the nucleic acids, after selective amplification, to an assay chamber on the assay portion.

FIG. 10 shows active regions of fluid movement in cartridge 14 during transfer of amplified nucleic acids 147 to assay chamber 68 of assay portion 44. Fluid flows along fluid path 148 from a chamber 52 that holds wash solution B to assay chamber 68. Fluid path 148 may be activated by opening valve 150 and vent-valve 122. Overfilling assay chamber 68 may be restricted, for example, by vent 108 on vent-valve 122, or by a sensor that monitors fluid position and signals the closing of valve 150, among others. As described above, nucleic acids 127 and amplified target nucleic acids 147 may be transferred by fluid flow and/or electrophoretically using electrodes disposed in assay chamber 68 (see below). In some embodiments, amplification chamber 66 first may be equilibrated with wash solution B by closing vent-valve 122 and opening valves 140, 150, thus directing wash solution B through amplification chamber 66, concentration chamber 64, and into waste chamber B. Alternatively, or in addition, amplified nucleic acid(s) 147 may be transferred electrophoretically to an assay chamber 68 preloaded with assay solution.

Amplified target nucleic acid(s) 147 (and isolated nucleic acids 127) may be assayed in assay chamber 68. For example, assay chamber 68 may include one or more positioned receptors (a positional array) for nucleic acid identification and/or quantification, as described in Section II. Hybridization of amplified nucleic acids 147 to receptors may be assisted by electrodes positioned near to the receptors in assay chamber 68. The electrodes may be biased positively in a sequential manner to direct the amplified nucleic acids to individual members (or subgroups) of the array. After electrophoretically moving amplified target nucleic acid(s) 147 to many or all positions of the array, to allow specific binding or hybridization, unbound or unhybridized nucleic acid(s) may be removed electrophoretically and/or by fluid flow (not shown here).

FIGS. 11 and 12 show selected aspects of assay portion 44, viewed in plan from external cartridge 14 and in cross-section, respectively. Assay portion 44 includes a substrate portion 158. Substrate portion 158 at least partially defines fluid compartments of the assay portion. The substrate portion may include a substrate 160. The substrate portion also may include electronic circuitry 58 and/or thin-film layers formed on the substrate and disposed near a surface 162 of the substrate. Thin-film electronic devices of the circuitry and fluid compartments of network 48 each may be disposed near a common surface of the substrate so that the electronic devices are closely apposed to, and/or in fluid contact with, regions of the fluid network. Thus, the thin-film devices may be configured to modify and/or sense a property of fluid (or sample/analyte) in fluid network 48. An exemplary material for substrate 160 is silicon, typically monocrystalline silicon. Other suitable substrate materials and properties are described below in Section II.

Fluid network 48 or a fluidically connected fluid space of one or more fluid compartments may be cooperatively defined near a surface 162 of the substrate using substrate portion 158 and a fluid barrier 163. The fluid space may determine total fluid capacity for holding fluid between the substrate portion and the fluid barrier. The term "cooperatively defined" means that the fluid space, or a fluid compartment thereof, is disposed substantially (or completely) between substrate portion 158 and fluid barrier 163. Fluid barrier 163 may be any structure that prevents substantial escape or exit of fluid out of the device, through the barrier, from fluid network 48, or a compartment thereof. Preventing substantial exit of fluid from the cartridge means that drops, droplets, or a stream of fluid does not leave the device through the fluid barrier. Accordingly, the fluid barrier may be free of openings that fluidically connect fluid network 48 to regions exterior to the device. The fluid barrier also may fluidically seal a perimeter defined at the junction between the fluid barrier and the substrate portion to prevent substantial exit of fluid from the cartridge at the junction. Typically, the fluid barrier also restricts evaporative loss from fluid network 48.

Fluid network 48 may be formed as follows. Surface 162 of substrate 160 and/or circuitry 58 may define a base wall 164 of fluid network 48. A patterned channel layer 166 may be disposed over surface 162 and base wall 164 to define side walls 168. Channel layer 166 may be formed from any suitable material, including, but not limited to, a negative or positive photoresist (such as SU-8 or PLP), a polyimide, a dry film (such as DuPont Riston), and/or a glass. Methods for patterning channel layer 166 may include photolithography, micromachining, molding, stamping, laser etching, and/or the like. A cover 170 may be disposed on channel layer 166, and spaced from base 164, to seal a top region of fluid network 48 that is spaced from electronic circuitry 58 (see FIG. 12). Cover 170 may be a component separate from channel layer 166, such as a layer that is bonded or otherwise attached to channel layer 166, or may be formed integrally with channel layer 166. In either case, fluid barrier 163 may include an opposing wall 171 that is sealed against fluid movement and escape from the cartridge. Cover 170 may be transparent, for example, glass or clear plastic, when assays are detected optically through the cover. Alternatively, cover 170 may be optically opaque, for example, when assays are detected electrically. Fluid network 48 may include spatially distinct chambers 64, 66, 68, as described above, to carry out distinct processes, and/or distinct processes may be carried out in a shared fluid compartment.

At least a thin-film portion of circuitry 58 may be formed above, and carried by, surface 162 of substrate 160. The circuitry typically includes thin-film layers that at least partially define one or more electronic circuit. The circuitry may include electrodes 172 that contact fluid in fluid network 48. Electrodes and other thin-film devices (see Section II) may be electrically coupled to electrical contact pads 174 (see FIG. 11), generally through semiconductor circuitry (including signal processing circuitry) formed on the substrate, that is, fabricated on and/or below surface 162. A given number of contact pads 174 may control a substantially greater number of electrodes and/or other thin-film devices. In preferred embodiments, contact pads 174 are electrically coupled to contacts 18, such as with a flexible circuit.

Electrodes 172 may have any suitable composition, distribution, and coating. Suitable materials for electrodes 172 are conductive materials, such as metals, metal alloys, or metal derivatives. Exemplary electrode materials include, gold, platinum, copper, aluminum, titanium, tungsten, metal silicides, and/or the like. Circuitry 58 may include electrodes at one or plural sites along base 164 of fluid network 48. For example, as shown here, electrodes may be arrayed as plural discrete units, either in single file along a channel/chamber, as in concentrator 64, and/or in a two-dimensional array, as in chambers 66, 68. Alternatively, or in addition, electrodes 172 may be elongate or have any other suitable shape or shapes. Each electrode 172 may be biased electrically on individual basis, either positively or negatively, so that nucleic acids are attracted to, or repelled from, the electrode, or the electrode may be electrically unbiased. Electrical biasing may be carried out in any suitable spatially and time-regulated manner by control apparatus 12 and/or cartridge 14, based on desired retention and/or directed movement of nucleic acids. Electrodes 172 may be coated with a permeation layer to allow access of fluid and ions to the electrode in the fluid compartment, but to exclude larger molecules (such as nucleic acids) from direct contact with the electrodes. Such direct contact may chemically damage the nucleic acids. Suitable electrode coatings may include hydrogels and/or sol-gels, among others, and may be applied by any suitable method, such as sputtering, spin-coating, etc. Exemplary materials for coatings may include polyacrylamides, agaroses, and/or synthetic polymers, among others.

Assay portion 44 is fluidically connected to fluid-handling portion 42. Any suitable interface passage (or a single passage) may be used for this connection to join fluid networks 46, 48 of the cartridge. Such fluid connection may allow fluid to be routed in relation to a fluid compartment, that is, to and/or from the fluid compartment.

Fluid networks 46, 48 may be separated spatially by substrate 160 and/or fluid barrier 163. When separated by substrate 160, interface passages may extend through substrate 160, generally between surface 162 of substrate 160 and opposing surface 176, to join the fluid networks. Interface passages may be described as feed structures to define paths for fluid movement. Alternatively, or in addition, one or more interface channels may extend around an edge 178 (FIG. 11) of substrate 160 to connect to fluid network 46 (FIGS. 5-10). For example, interface channels may extend through channel layer 166 and/or cover 170, but sealed against substantial exit of fluid from the cartridge. In alternative embodiments, fluid networks 46, 48 may be separated spatially by fluid barrier 163 rather than substrate 160, with some or all interface channels again extending through fluid barrier 163 to connect fluidly to fluid network 46.

In the depicted embodiment, interface passages, labeled 180a through 180e, extend through substrate 160 between opposing surfaces of the substrate (see FIGS. 10-12). An interface passage 180 may fluidly connect any fluid compartment of the fluid-handling portion to a fluid compartment of fluid network 48, generally by directly linking to fluid conduits or chambers of the two portions. For example, an interface passage 180 may connect a reagent reservoir 52 to a chamber (64-68) of assay portion 44, a chamber of the assay portion to a waste chamber, pre-processing chamber 120 to a chamber of the assay portion, two or more chambers of the assay portion to each other (not shown), a sample input site 50 directly to a chamber of the assay portion (also not shown), and/or a chamber of the assay portion to a valve and/or vent (such as valve-vent 122), among others. Each individual compartment of the assay portion may connect directly to any suitable number of interface passages 180. Here, concentration chamber 64 has three, 180a-180c, and amplification chamber 66 and assay chamber 68 each have one, 180d and 180e, respectively.

FIG. 12 shows how interface passage 180e fluidly connects assay portion 44 to fluid-handling portion 42. Interface passage 180e is configured to carry fluid along fluid path 182, from assay chamber 68 to valve-vent 122 (see FIG. 10). The interface passage may carry fluid to a channel (or channels) 104 of fluid-handling portion 42. Each channel 104 may be connected to an interface passage 180 through a fluid manifold 184 that directs fluid to one or plural channels 104 in fluid-handling portion 42, and to one or plural fluid compartments in assay portion 44. Accordingly, assay portion 44 may be attached fixedly to fluid manifold 184, for example, by using an adhesive 186.

An interface passage may have a diameter that varies along its length (measured generally parallel to direction of fluid flow). For example, the diameter of interface passage 180e may be smaller adjacent surface 162 of substrate 160, at an end region of the channel, than within an intermediate region defined by substrate 160, to form an opening 188 for routing fluid. The opening routes fluid by directing fluid to and/or from a fluid compartment. Opening 188 typically adjoins a fluid compartment. The fluid compartment is defined at least partially by the fluid barrier and may be configured so that fluid cannot exit the microfluidic device locally from the compartment, that is, directly out through the fluid barrier. The fluid compartment may be defined cooperatively between the substrate portion and the fluid barrier. The opening may include a perimeter region that forms an overhang (or shelf) 192 in which film layers 190 do not contact substrate 160. Opening 188 may have any suitable diameter, or a diameter of about 1 μm to 100 μm. The opening or hole may provide more restricted fluid flow than the substrate-defined region of the interface passage alone. Opening 188 may be defined by an opening formed in one or more film layers 190 formed on surface 162 of substrate 160. Film layers 190 typically are thin, that is, substantially thinner than the thickness of substrate 160, and may have a thickness and/or functional role as described in Section II.

FIGS. 13-19 show stepwise formation of interface passage 180e, opening 188, and assay chamber 68, in assay portion 44, using an exemplary method for fabrication of the assay portion. The method includes film deposition and patterning steps. Here, patterning generally refers to the process of patterned removal of a film layer after, for example, selective exposure of regions of the film layer to light.

FIG. 13 shows a suitable starting material for the assay portion: a substantially planar substrate 160, with opposing surfaces 162, 176. The method described here may be carried out with a silicon substrate that is thin, for example, having a thickness of about 0.1 to 2 mm, or 0.2 to 1 mm. The substrate may be modified at surface 162, during and/or after, but typically before addition of film layers 190, to include n- and p-doped regions that form transistors, FETS, bipolar devices, and/or other semiconductor electronic devices (not shown).

FIG. 14 shows the assay portion after application and patterning of film layers 190 on surface 162 of substrate 160. Film layers 190 may include any suitable films used to form and/or protect conductive portions of circuitry 58. Film layers may be formed of conductive material (for example, to form electrodes and conductive connections between devices), semiconductive material (for example, to form transistors using n- and p-doped material), and/or insulating material (for example, passivation layers). Film layers may be applied and patterned by conventional methods. At least one of film layers 190 may be patterned to define perimeter 194 of opening 188.

FIG. 15 shows the assay portion after unpatterned channel layer 196 has been disposed on film layers 190 and opening 188. Channel layer 196 may be applied at an appropriate thickness, typically a thickness of about 1-200 μm, more typically 2-100 μm, or even 5-50 μm. Exemplary materials for channel layer 196 (and the fluid barrier) are described above.

FIG. 16 shows the assay portion after an etch mask 198 has been added to opposing surface 176 of substrate 160. The etch mask may be applied as a layer of appropriate thickness, and selectively removed at a localized region (or regions) to define opening 200. Opening 200 may have any suitable diameter, but typically has a diameter greater than the diameter of opening 188. Opening 200 may be disposed opposite opening 188 so that a projection of aperture 200 onto film layers 190 forms a corresponding channel or through-hole 201 in the substrate that may encompass opening 188 circumferentially.

FIG. 17 shows the assay portion after formation of the substrate region of interface passage 180e, and after removal of etch mask 198. Substrate 160 may be etched generally orthogonally from surface 176 along a volume defined by aperture 200 (see FIG. 16) to produce channel 201. Any suitable etching procedure may be used to form the substrate portion of interface passage 180e. However, deep-reactive ion etching (DRIE) typically is used. One or more layers of film layers 190 may act as an etch stop, so that overhang region 192 is formed. After etching, the mask may be stripped from opposing surface 176 or left on the surface.

FIG. 18 shows the assay portion after regions of the unpatterned channel layer 196 have been selectively removed to form patterned channel layer 166. Selective removal may be carried out by any appropriate process, for example, photopatterning layer 196 followed by development of the photopatterned layer, or laser ablation.

FIG. 19 shows the completed assay portion 44 after attachment of cover 170, but prior to affixing the assay portion to fluid-handling portion 42 through manifold 184. Cover 170 may be attached to fluid barrier 166 by any suitable method, such as with an adhesive, heat and pressure application, anodic bonding, sonic welding, and/or conventional methods.

FIG. 20 shows a somewhat schematic representation of an intra-chip passage 202 formed in assay portion 204. Intra-chip passage 202 may enter and exit substrate 160 from surface 162 through openings 188, without extending to opposing surface 176. Therefore, intra-chip passage 202 is distinct from interface passages 180 that extend between cartridge portions 42, 44. Intra-chip passage(s) 202 may be used to route fluid between chambers 206 defined cooperatively by substrate portion 158 and fluid barrier 208. Alternatively, or in addition, intra-chip passages may be used to mix fluid (see below), to perform a reaction or assay, and/or the like.

FIGS. 21-23 show stepwise formation of intra-chip passage 202 in assay portion 204 using an exemplary method. Materials and process steps are generally as described above for FIGS. 12-19. FIG. 21 shows a stage of fabrication after film layers 190 have been formed on surface 162 of substrate 160 and patterned to form plural openings 188. FIG. 22 shows the assay portion after anisotropic etching of substrate 160 under openings 188 to form a substrate recess or trough 210. Alternatively, trough 210 may be formed by isotropic etching. In either case, etchant may access substrate 160 through openings 188 to undercut film layers 190, thus joining local recesses 212, disposed under each opening 188, to form trough 210. Accordingly, openings 188 typically are spaced closely enough to allow recesses 212 to be connected fluidically during etching of substrate 160. FIG. 23 shows assay portion 204 after formation of chambers 206 using fluid barrier 208. Here, fluid barrier 208 includes channel layer 166, to define chamber side walls, and cover 170, to seal the top of chambers 206. One or more of openings 188 defined by film layers 190 and used to form trough 210 may be blocked by channel layer 166. For example, the central opening here has been sealed by channel layer 166, as shown at 214.

FIG. 24 shows an assay portion 216 having a manifold channel 218. Manifold channel 218 is a trans-substrate passage that connects fluidically to two or more openings 188 in thin films 190. Here, openings 188 fluidically connect manifold channel 218 to two chambers 206. However, manifold channel 218 may fluidically connect to any suitable number of compartments in the fluid network of the assay portion. Manifold channel 218 may be used to receive (or deliver) fluid from (or to) fluid-handling portion 42, for example, to deliver (or receive) fluid to (or from) one or both of chambers 206. Manifold channel 218 also may be used to direct fluid between chambers 206, as indicated in FIG. 20. An exemplary method for forming manifold channel 218 follows the procedure outlined in FIGS. 15-19, after formation of trough 210 in FIG. 22.

FIG. 25 shows a top plan, fragmentary view of an assay portion 230 that includes a mixing chamber 232. Mixing chamber 232 has a trough 234 similar to trough 210 of FIG. 22, formed under film layers at plural openings 236 (six inlet openings and one outlet opening are shown here). Trough 234 is fed from the fluid network of assay portion 230 by plural inlet channels 238, 240, which carry fluid into inlet openings along paths indicated by the arrows. Each channel may direct fluid, generally distinct fluids, into trough 234 using an interleaved geometry along the trough to allow mixing of the fluids from the plural channels within the trough. Mixed fluid exits trough 234, shown at 242, at an outlet opening 236 to direct fluid back into an outlet channel 244 of the fluid network of assay portion 230. In alternative embodiments, any suitable number of inlet and outlet channels may be connected to mixing chamber 232 through any suitable number of openings 236.

FIG. 26 shows selected portions of assay portion 44, particularly film layers 190, in more detail. Exemplary thin films may include a field oxide (FOX) layer 252, formed from substrate 160, and a phospho-silicate glass (PSG) layer 254 disposed over FOX layer 252. FOX layer 252 may provide a thermal barrier to thermally insulate heating effects. PSG layer 254 may be pulled back from opening 188, shown at 255, to avoid fluid contact with the PSG layer, which may have corrosive effects. Accordingly, PSG layer 254 defines a protected opening with a larger diameter than fluid-contacting opening 188. The thin films also may include a resistor layer 256, formed of any suitable resistive material, such as tantalum aluminum (TaAl). Current passes through the resistor layer 256 from connected conductors, formed of any appropriate conductive material, such as aluminum or an aluminum alloy (not shown). The resistor layer produces heat, which may be insulated from substrate 160 by FOX layer 252, among others. One or more passivation layers 258 may cover these thin films. Suitable materials for a passivation layer may include silicon nitride ($Si_3N_4$) or silicon carbide (SiC), among others. Additional electronic circuitry features, such as electrodes, transistors, and diodes, which may be disposed above and/or below the surface of the substrate, are not shown here.

II. Microfluidic Systems

Microfluidic systems are provided for sample manipulation and/or analysis. Microfluidic systems generally include devices and methods for receiving, manipulating, and analyzing samples in very small volumes of fluid (liquid and/or gas). The small volumes are carried by one or more fluid passages, at least one of which typically has a cross-sectional dimension or depth of between about 0.1 to 500 μm, or, more typically, less than about 100 μm or 50 μm. Microfluidic devices may have any suitable total fluid capacity. Accordingly, fluid at one or more regions within microfluidic devices may exhibit laminar flow with minimal turbulence, generally characterized by a low Reynolds number.

Fluid compartments may be fluidically connected within a microfluidic device. Fluidically connected or fluidically coupled generally means that a path exists within the device for fluid communication between the compartments. The path may be open at all times or be controlled by valves that open and close (see below).

Various fluid compartments may carry and/or hold fluid within a microfluidic device and are enclosed by the device. Compartments that carry fluid are passages. Passages may include any defined path or conduit for routing fluid movement within a microfluidic device, such as channels, processing chambers, apertures, or surfaces (for example, hydrophilic, charged, etc.), among others. Compartments that hold fluid for delivery to, or receipt from, passages are termed chambers or reservoirs. In many cases, chambers and reservoirs are also passages, allowing fluid to flow through the chambers or reservoirs. Fluid compartments within a microfluidic device that are fluidically connected form a fluid network or fluid space, which may be branched or unbranched. A microfluidic device, as described herein, may include a single fluidically connected fluid network or plural separate, unconnected fluid networks. With plural separate fluid networks, the device may be configured to receive and manipulate plural samples, at the same time and/or sequentially.

Chambers may be classified broadly as terminal and intermediate chambers. Terminal chambers generally may define as a starting point or endpoint for fluid movement within a fluid network. Such chambers may interface with the external environment, for example, receiving reagents during device manufacture or preparation, or may receive fluid only from fluid pathways within the microfluidic device. Exemplary terminal chambers may act as reservoirs that receive and/or store processed sample, reagents, and/or waste. Terminal chambers may be loaded with fluid before and/or during sample analysis. Intermediate chambers may have an intermediate position within a fluid network and thus may act as passages for processing, reaction, measurement, mixing, etc. during sample analysis.

Microfluidic devices may include one or more pumps to push and/or pull fluid or fluid components through fluid networks. Each pump may be a mechanically driven (pressure-mediated) pump or an electrokinetic pump, among others. Mechanically driven pumps may act by positive pressure to push fluid through the network. The pressure may be provided by a spring, pressurized gas (provided internally or external to the system), a motor, a syringe pump, a pneumatic pump, a peristaltic pump, and/or the like. Alternatively, or in addition, a pressure-driven pump may act by negative pressure, that is, by pulling fluid towards a region of decreased pressure. Electrokinetic or electrically driven pumps may use an electric field to promote flow of fluid and/or fluid components by electrophoresis, electroosmosis, electrocapillarity, and/or the like. In some embodiments, pumps may be micropumps fabricated by micromachining, for example, diaphragm-based pumps with piezoelectric-powered movement, among others.

Valves may be included in microfluidic devices described herein. A valve generally includes any mechanism to regulate fluid flow through a fluid network and may be a bi-directional valve, a check valve, and/or a vent, among others. For example, a valve may be used to block or permit fluid flow through a fluid passage, that is, as a binary switch, and/or to adjust the rate of fluid flow. Accordingly, operation of a valve may select a portion of a fluid network that is active, may isolate one or more portions of the fluid network, and/or may select a processing step that is implemented, among others. Therefore, valves may be positioned and operated to deliver fluid, reagents, and/or sample(s) from a fluid compartment to a desired region of a fluid network. Suitable valves may include movable diaphragms or membranes, compressible or movable passage walls, ball valves, sliding valves, flap valves, bubble valves, and/or immiscible fluids, among others. Such valves may be operated by a solenoid, a motor, pressure (see above), a heater, and/or the like.

Suitable valves may be microvalves formed on (or in) substrates along with thin-film electronic devices (see below) by conventional fabrication methods. Microvalves may be actuated by electrostatic force, piezoelectric force, and/or thermal expansion force, among others, and may have internal or external actuators. Electrostatic valves may include, for example, a polysilicon membrane or a polyimide cantilever that is operable to cover a hole formed in a substrate. Piezoelectric valves may include external (or internal) piezoelectric disks or beams that expand against a valve actuator. Thermal expansion valves may include a sealed pressure chamber bounded by a diaphragm. Heating the chamber causes the diaphragm to expand against a valve seat. Alternatively, thermal expansion valves may include a bubble valve. The bubble valve may be formed by a heater element that heats fluid to form a bubble in a passage so that the bubble blocks fluid flow through the passage. Discontinued heating collapses the bubble to allow fluid flow. Microvalves may be reversible, that is, capable of both closing and opening, or may be substantially irreversible, that is, single-use valves capable of only opening or closing. An exemplary single-use valve is a heat-sensitive obstruction in a fluid passage, for example, in a polyimide layer. Such an obstruction may be destroyed or modified upon heating to allow passage of fluid.

Vents may be used, for example, to allow release of displaced gas that results from fluid entering a fluid compartment. Suitable vents may include hydrophobic membranes that allow gas to pass but restrict passage of hydrophilic liquids. An exemplary vent is a GORETEX membrane.

A microfluidic device, as described herein, may be configured to perform or accommodate three steps: inputting, processing, and outputting. These steps are generally performed in order, for a given sample, but may be performed asynchronously when plural samples are inputted into the device.

Inputting allows a user of the microfluidic device to introduce sample(s) from the external world into the microfluidic device. Accordingly, inputting requires an interface(s) between the external world and the device. The interface thus typically acts as a port, and may be a septum, a valve, and/or the like. Alternatively, or in addition, sample(s) may be formed synthetically from reagents within the device. Reagents may be introduced by a user or during manufacture of the device. In a preferred embodiment, the reagents are introduced and sealed into the device or cartridge during manufacture.

The inputted sample(s) is then processed. Processing may include any sample manipulation or treatment that modifies a physical or chemical property of the sample, such as sample composition, concentration, and/or temperature. Processing may modify an inputted sample into a form more suited for analysis of analyte(s) in the sample, may query an aspect of the sample through reaction, may concentrate the sample, may increase signal strength, and/or may convert the sample into a detectable form. For example, processing may extract or release (for example, from cells or viruses), separate, purify, concentrate, and/or enrich (for example, by amplification) one or more analytes from an inputted sample. Alternatively, or in addition, processing may treat a sample or its analyte(s) to physically, chemically, and/or biologically modify the sample or its analyte(s). For example, processing may include chemically modifying the sample/analyte by labeling it with a dye, or by reaction with an enzyme or substrate, test reagent, or other reactive materials. Processing, also or alternatively, may include treating the sample/analyte(s) with a biological, physical, or chemical condition or agent. Exemplary conditions or agents include hormones, viruses, nucleic acids (for example, by transfection), heat, radiation, ultrasonic waves, light, voltage pulse(s), electric fields, particle irradiation, detergent, pH, and/or ionic conditions, among others. Alternatively, or in addition, processing may include analyte-selective positioning. Exemplary processing steps that selectively position analyte may include capillary electrophoresis, chromatography, adsorption to an affinity matrix, specific binding to one or more positioned receptors (such as by hybridization, receptor-ligand interaction, etc.), by sorting (for example, based on a measured signal), and/or the like.

Outputting may be performed after sample processing. A microfluidic device may be used for analytical and/or preparative purposes. Thus, the step of outputting generally includes obtaining any sample-related signal or material from the microfluidic device.

Sample-related signals may include a detectable signal that is directly and/or indirectly related to a processed sample and measured from or by the microfluidic device. Detectable signals may be analog and/or digital values, single or multiple values, time-dependent or time-independent values (e.g., steady-state or endpoint values), and/or averaged or distributed values (e.g., temporally and/or spatially), among others.

The detectable signal may be detected optically and/or electrically, among other detection methods. The detectable signal may be an optical signal(s), such as absorbance, luminescence (fluorescence, electroluminescence, bioluminescence, chemiluminescence), diffraction, reflection, scattering, circular dichroism, and/or optical rotation, among others. Suitable fluorescence methods may include fluorescence resonance energy transfer (FRET), fluorescence lifetime (FLT), fluorescence intensity (FLINT), fluorescence polarization (FP), total internal reflection fluorescence (TIRF), fluorescence correlation spectroscopy (FCS), fluorescence recovery after photobleaching (FRAP), and/or fluorescence activated cell sorting (FACS), among others. Optical signals may be measured as a nonpositional value, or set of values, and/or may have spatial information, for example, as measured using imaging methods, such as with a charge-coupled device. In some embodiments, the detectable signal may be an optoelectronic signal produced, for example, by an onboard photodiode(s). Other detectable signals may be measured by surface plasmon resonance, nuclear magnetic resonance, electron spin resonance, mass spectrometry, and/or the like. Alternatively, or in addition, the detectable signal may be an electrical signal(s), that is, a measured voltage, resistance, conductance, capacitance, power, etc. Exemplary electrical signals may be measured, for example, across a cell membrane, as a molecular binding event(s) (such as nucleic acid duplex formation, receptor-ligand interaction, etc.), and/or the like.

In some embodiments, the microfluidic device may be used for sample preparation. Sample-related material that may be outputted includes any chemical or biological compound(s), polymer(s), aggregate(s), mixture(s), assembli(es), and/or organism(s) that exits the device after processing. Such sample-related material may be a chemically modified (synthetic), biologically modified, purified, and/or sorted derivative, among others, of an inputted sample.

The microfluidic device may include distinct structural portions for fluid handling (and storage) and for conducting assays, as exemplified in Section I. These portions may be configured to carry out distinct processing and/or manipulation steps. The fluid-handling portion may be formed separately from the assay portion and may have a fluid network or fluid space that is more three-dimensional than the fluid network or fluid space of the assay portion. The fluid-handling portion may have fluid chambers with any suitable volume, including one or more chambers with a fluid capacity of tens or hundreds of microliters up to about five milliliters or more.

The fluid-handling portion may include a sample input site(s) (port) to receive sample, and plural fluid reservoirs to hold and deliver reagents and/or to receive waste. The fluid-handling portion may be dimensioned for somewhat larger volumes of fluid, in some cases, volumes of greater than one microliter or one milliliter. In addition, the fluid-handling portion may include a pre-processing site(s), formed by one or more fluid passages, to separate an analyte(s) of interest from waste material, for example, to isolate analytes (such as nucleic acids) from a sample that includes one or plural cells. The fluid-handling portion may define a generally nonplanar fluid network or fluid space. In a nonplanar or three-dimensional fluid network, one or more portions of the fluid network may be disposed greater than two millimeters from any common plane.

The assay portion may provide a site at which final sample processing occurs and/or assay signals are measured. The assay portion may be configured for manipulation and analysis of smaller sample volumes, generally having fluid chambers less than about 50 microliters, preferably less than about 10 microliters, and more preferably less than about one microliter.

The assay portion may be distinct from the fluid-handling portion, that is, formed of distinct components not shared with the fluid-handling portion. Accordingly, the assay portion may be formed separately, and then attached to the fluid-handling portion to fluidly connect fluid compartments of the portions.

The assay portion may include a substrate portion and a fluid barrier. The electronic circuitry may be disposed at least partially or at least substantially between the substrate portion and the fluid barrier. The substrate portion may cooperatively define a fluid space with the fluid barrier near a surface of the substrate portion. The electronic circuitry may include the thin-film portions or layers of an electronic circuit (or circuits), in which the thin-film layers also are disposed near the surface of the substrate. A structure that is near or proximate the surface is closer to the substrate surface than to an opposing surface of the substrate.

The electrical properties of the substrate may determine where the electronic circuitry, particularly solid-state electronic switching devices, is positioned relative to the substrate and the fluid barrier. The substrate may be a semiconductor so that some portions of the electronic circuitry are created within the substrate, for example, by n- and p-doping. Alternatively, the substrate may be an insulator. In this case, all of the electronic circuitry may be carried external to the substrate. A suitable substrate may be generally flat or planar on a pair of opposing surfaces, for example, to facilitate deposition of thin films. The substrate may be at least substantially inorganic, including as silicon, gallium arsenide, germanium, glass, ceramic, alumina, and/or the like.

Thin-film electronic circuitry includes thin films or thin-film layers. Each thin-film layer of the electronic circuitry may play a direct or auxiliary role in operation of the circuitry, that is, a conductive, insulating, resistive, capacitive, gating, and/or protective role, among others. The protective and/or insulating role may provide electrical insulation, chemical insulation to prevent fluid-mediated corrosion, and/or the like. The thin-film layers may have a thickness of less than about 100 µm, 50 µm, or 20 µm. Alternatively, or in addition, the thin-film layers may have a thickness of greater than about 10 nm, 20 nm, or 50 nm. Such thin films form electronic devices, which are described as electronic because they are controlled electronically by the electronic circuitry of the assay portion. The electronic devices are configured to modify and/or sense a property of fluid within a fluid compartment of the assay portion. Thus, the electronic devices and portions of the thin-film layers may be disposed between the substrate and the fluid network or compartment of the assay portion. Exemplary modifying devices include electrodes, heaters (for example, resistors), coolers, pumps, valves, and/or so on. Accordingly, the modified property may be analyte distribution or position within the fluid or fluid compartment, analyte mobility, analyte concentration, analyte abundance relative to related sample components, fluid flow rate, fluid isolation, or fluid/analyte temperature, among others. Alternatively, or in addition, thin-film devices may monitor or sense fluid and/or analyte conditions or positions. Exemplary sensing devices may include temperature sensors, flow-rate sensors, pH sensors, pressure sensors, fluid sensors, optical sensors, current sensors, voltage sensors, analyte sensors, and/or the like. Combining a modifying and a sensing device may allow feedback control, for example, closed loop temperature control of a fluid region within the assay portion.

Electronic circuitry included in the assay portion is flexible, in contrast to electrical circuits that respond linearly. Electronic circuits use semiconductor devices (transistors, diodes, etc.) and solid-state electronic switching so that a smaller number of input-output lines can connect electrically to a substantially greater number of electronic devices. Accordingly, the electronic circuitry may be connected to and/or may include any suitable combination of input and output lines, including power/ground lines, data input lines, fire pulse lines, data output lines, and/or clock lines, among others. Power/ground lines may provide power to modifying and sensing devices. Data input lines may provide data indicative of devices to be turned on (for example, a heater(s) or electrode(s)). Fire pulse lines may be supplied externally or internally to the chip. These lines may be configured to cause activation of a particular set of data for activating modifying and/or sensing devices. Data output lines may receive data from circuitry of the assay portion, for example, digital data from sensing devices. Based on the rate of data input and output, a single data input/output line or plural data input/output lines may be provided. With a low data rate, the single data input/output line may be sufficient, but with a higher rate, for example, to drive plural thin-film devices in parallel, one or more data input lines and a separate data input/output line may be necessary. Clock lines may provide timing of processes, such as sending and receiving data from a controller (see below).

A microfluidic device may be configured to be controlled by a control apparatus or controller. Accordingly, the microfluidic device is electrically coupled to the controller, for example, conductively, capacitively, and/or inductively. The controller may provide any of the input and/or output lines described above. In addition, the controller may provide a user interface, may store data, may provide one or more detectors, and/or may provide a mechanical interface, Exemplary functions of the controller include operating and/or providing valves, pumps, sonicators, light sources, heaters, coolers, and/or so on, in order to modify and/or sense fluid, sample, and/or analyte in the microfluidic device.

Further aspects of microfluidic devices, fluid-handling portions, assay portions, and controllers, among others, are described above in Section I.

III. Samples

Microfluidic systems, as described herein, are configured to process samples. A sample generally includes any material of interest that is received and processed by a microfluidic system, either to analyze the material of interest (or analyte) or to modify it for preparative purposes. The sample generally has a property or properties of interest to be measured by the system or is advantageously modified by the system (for example, purified, sorted, derivatized, cultured, etc.). The sample may include any compound(s), polymer(s), aggregate(s), mixture(s), extract(s), complex(es), particle(s), virus(es), cell(s), and/or combination thereof. The analytes and/or materials of interest may form any portion of a sample, for example, being a major, minor, or trace component in the sample.

Samples, and thus analytes contained therein, may be biological. Biological samples generally include cells, viruses, cell extracts, cell-produced or -associated materials, candidate or known cell modulators, and/or man-made variants thereof. Cells may include eukaryotic and/or prokaryotic cells from any single-celled or multi-celled organism and may be of any type or set of types. Cell-produced or cell-associated materials may include nucleic acids (DNA or RNA), proteins (for example, enzymes, receptors, regulatory factors, ligands, structural proteins, etc.), hormones (for example, nuclear hormones, prostaglandins, leukotrienes, nitric oxide, cyclic nucleotides, peptide hormones, etc.), carbohydrates (such as mono-, di-, or polysaccharides, glycans, glycoproteins, etc.), ions (such as calcium, sodium, potassium, chloride, lithium, iron, etc.), and/or other metabolites or cell-imported materials, among others.

Biological samples may be clinical samples, research samples, environmental samples, forensic samples, and/or industrial samples, among others. Clinical samples may include any human or animal samples obtained for diagnostic and/or prognostic purposes. Exemplary clinical samples may include blood (serum, whole blood, or cells), lymph, urine, feces, gastric contents, bile, semen, mucus, a vaginal smear, cerebrospinal fluid, saliva, perspiration, tears, skin, hair, a tissue biopsy, a fluid aspirate, a surgical sample, a tumor, and/or the like. Research samples may include any sample related to biological and/or biomedical research, such as cultured cells or viruses (wild-type, engineered, and/or mutant, among others.), extracts thereof, partially or fully purified cellular material, material secreted from cells, material related to drug screens, etc. Environmental samples may include samples from soil, air, water, plants, and/or man-made structures, among others, being analyzed or manipulated based on a biological aspect.

Samples may be nonbiological. Nonbiological samples generally include any sample not defined as a biological sample. Nonbiological samples may be analyzed for presence/absence, level, size, and/or structure of any suitable inorganic or organic compound, polymer, and/or mixture. Suitable nonbiological samples may include environmental samples (such as samples from soil, air, water, etc.), synthetically produced materials, industrially derived products or waste materials, and/or the like.

Samples may be solid, liquid, and/or gas. The samples may be pre-processed before introduction into a microfluidic system or may be introduced directly. Pre-processing external to the system may include chemical treatment, biological treatment (culturing, hormone treatment, etc.), and/or physical treatment (for example, with heat, pressure, radiation, ultrasonic disruption, mixing with fluid, etc.). Solid samples (for example, tissue, soil, etc.) may be dissolved or dispersed in fluid before or after introduction into a microfluidic device and/or analytes of interest may be released from the solid samples into fluid within the microfluidic system. Liquid and/or gas samples may be pre-processed external to the system and/or may be introduced directly.

IV. Assays

Microfluidic systems may be used to assay (analyze/test) an aspect of an inputted sample. Any suitable aspect of a biological or nonbiological sample may be analyzed by a microfluidic system. Suitable aspects may relate to a property of one or more analytes carried by the sample. Such properties may include presence/absence, level (such as level of expression of RNA or protein in cells), size, structure, activity (such as enzyme or biological activity), location within a cell, cellular phenotype, and/or the like. Structure may include primary structure (such as a nucleotide or protein sequence, polymer structure, isomer structure(s), or a chemical modification, among others), secondary or tertiary structure (such as local folding or higher order folding), and/or quaternary structure (such as intermolecular interactions). Cellular phenotypes may relate to cell state, electrical activity, cell morphology, cell movement, cell identity, reporter gene activity, and/or the like.

Microfluidic assays may measure presence/absence or level of one or more nucleic acid. Each nucleic acid analyzed may be present as a single molecule or, more typically, plural molecules. The plural molecules may be identical or substantially identical and/or may share a region, generally of twenty or more contiguous bases, that is identical. As used herein, a nucleic acid (nucleic acid species) generally includes a nucleic acid polymer or polynucleotide, formed as a chain of covalently linked monomer subunits. The monomer subunits may form polyribonucleic acids (RNA) and/or polydeoxyribonucleic acids (DNA) including any or all of the bases adenine, cytosine, guanine, uracil, thymine, hypoxanthine, xanthine, or inosine. Alternatively, or in addition, the nucleic acids may be natural or synthetic derivatives, for example, including methylated bases, peptide nucleic acids, sulfur-substituted backbones, and/or the like. Nucleic acids may be single, double, and/or triple-stranded, and may be wild-type, or recombinant, deletion, insertion, inversion, rearrangement, and/or point mutants thereof.

Nucleic acid analyses may include testing a sample to measure the presence/absence, quantity, size, primary sequence, integrity, modification, and/or strandedness of one or more nucleic acid species (DNA and/or RNA) in the sample. Such analyses may provide genotyping information and/or may measure gene expression from a particular gene (s) or genetic region(s), among others.

Genotyping information may be used for identification and/or quantitation of microorganisms, such as pathogenic species, in a sample. Exemplary pathogenic organisms may include, but are not limited to, viruses, such as HIV, hepatitis virus, rabies, influenza, CMV, herpesvirus, papilloma viruses, rhinoviruses; bacteria, such as *S. aureus, C. perfringens, V. parahaemolyticus, S. typhimurium, B. anthracis, C. botulinum, E. coli*, and so on; fungi, such as those included in the genuses *Candida, Coccidioides, Blastomyces, Histoplasma, Aspergillus, Zygomycetes, Fusarium* and *Trichosporon*, among others; and protozoans, such as Plasmodia (for example, *P. vivax, P. falciparum*, and *P. malariae*, etc.), *G. lamblia, E. histolitica*, Cryptosporidium, and *N. fowleri*, among others. The analysis may determine, for example, if a person, animal, plant, food, soil, or water is infected with or carries a particular microorganism(s). In some cases, the analysis may also provide specific information about the particular strain(s) present.

Genotyping analysis may include genetic screening for clinical or forensic analysis, for example, to determine the presence/absence, copy number, and/or sequence of a particular genetic region. Genetic screening may be suitable for prenatal or postnatal diagnosis, for example, to screen for birth defects, identify genetic diseases and/or single-nucleotide polymorphisms, or to characterize tumors. Genetic screening also may be used to assist doctors in patient care, for example, to guide drug selection, patient counseling, etc. Forensic analyses may use genotyping analysis, for example, to identify a person, to determine the presence of a person at a crime scene, or to determine parentage, among others. In some embodiments, nucleic acids may carry and/or may be analyzed for single nucleic polymorphisms.

Microfluidic systems may be used for gene expression analysis, either quantitatively (amount of expression) or qualitatively (expression present or absent). Gene expression analysis may be conducted directly on RNA, or on complementary DNA synthesized using sample RNA as a template, for example, using a reverse transcriptase enzyme. The complementary DNA may be synthesized within a microfluidic device, such as the embodiment described in Section I, for example, in the assay portion, or external to the device, that is, prior to sample input.

Expression analysis may be beneficial for medical purposes or research purposes, among others. For example, expression analysis of individual genes or sets of genes (profiling) may be used to determine or predict a person's health, guide selection of a drug(s) or other treatment, etc. Alternatively, or in addition, expression may be useful in research applications, such as reporter gene analysis, screening libraries (for example, libraries of chemical compounds, peptides, antibodies, phage, bacteria, etc.), and/or the like.

Assays may involve processing steps that allow a property of an analyte to be measured. Such processing steps may include labeling, amplification, binding to a receptor(s), and/or so on.

Labeling may be carried out to enhance detectability of the analyte. Suitable labels may be covalently or noncovalently coupled to the analyte and may include optically detectable dyes (fluorophores, chromophores, energy transfer groups, etc.), members of specific binding pairs (SBPs, such as biotin, digoxigenin, epitope tags, etc.; see Table 1), and/or the like. Coupling of labels may be conducted by an enzymatic reaction, for example, nucleic acid-templated replication (or ligation), protein phosphorylation, and/or methylation, among others, or may be conducted chemically, biologically, or physically (for example, light- or heat-catalyzed, among others).

For nucleic acid analyses, amplification may be performed to enhance sensitivity of nucleic acid detection. Amplification is any process that selectively increases the abundance (number of molecules) of a target nucleic acid species, or a region within the target species. Amplification may include thermal cycling (for example, polymerase chain reaction, ligase chain reaction, and/or the like) or may be isothermal (for example, strand displacement amplification). Further aspects of amplification are described above in Section I.

Receptor binding may include contacting an analyte (or a reaction product templated by, or resulting from, the presence of the analyte) with a receptor that specifically binds the analyte. The receptor(s) may be attached to, or have a fixed position within, a microfluidic compartment, for example, in an array, or may be distributed throughout the compartment. Specific binding means binding that is highly selective for the intended partner in a mixture, generally to the exclusion of binding to other moieties in the mixture. Specific binding may be characterized by a binding coefficient of less than about $10^{-4}$ M, and preferred specific binding coefficients are less than about $10^{-5}$ M, $10^{-7}$ M, or $10^{-9}$ M. Exemplary specific binding pairs that may be suitable for receptor-analyte interaction are listed below in Table 1.

TABLE 1

Representative Specific Binding Pairs

| First SBP Member | Second SBP Member |
|---|---|
| biotin | avidin or streptavidin |
| antigen | antibody |
| carbohydrate | lectin or carbohydrate receptor |
| DNA | antisense DNA; protein |
| enzyme substrate | enzyme; protein |
| histidine | NTA (nitrilotriacetic acid) |
| IgG | protein A or protein G |
| RNA | antisense or other RNA; protein |

Further aspects of sample assays, particularly assay of nucleic-acid analytes in samples, are described above in Section I.

It is believed that the disclosure set forth above encompasses multiple distinct embodiments of the invention. While each of these embodiments has been disclosed in specific form, the specific embodiments thereof as disclosed and illustrated herein are not to be considered in a limiting sense as numerous variations are possible. The subject matter of this disclosure thus includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

What is claimed is:

1. A device for performing microfluidic processing of a sample, comprising:
 a substrate defining a channel;
 a fluid barrier connected to the substrate such that a chamber is formed between the substrate and the fluid barrier, the fluid barrier providing side walls and an opposing wall of the chamber opposite the substrate, the fluid barrier being configured such that local exit of fluid out of the device from the chamber through the opposing wall is not permitted; and
 a plurality of thin-film layers disposed between the substrate and the fluid barrier, the thin-film layers including at least one thin-film layer defining a discrete opening that disposes the channel and the chamber in fluid communication and that routes fluid between the channel and the chamber, the thin-film layers providing at least one thin-film electronic device configured to process the sample in the chamber.

2. The device of claim 1, wherein the at least one thin-film electronic device includes at least one heater, at least one sensor, at least one electrode, or a combination thereof.

3. The device of claim 1, wherein the chamber is a concentration chamber, an amplification chamber, an assay chamber, or a combination thereof.

4. The device of claim 1, wherein the substrate includes opposing surfaces, and wherein the channel extends to each of the opposing surfaces.

5. The device of claim 1, wherein the at least one thin-film layer defines at least two openings, and wherein the channel extends to each of the at least two openings.

6. The device of claim 5, wherein the fluid barrier is connected to the substrate such that a plurality of chambers are formed between the substrate and the fluid barrier, and wherein a pair of the chambers are in fluid communication via the at least two openings and the channel.

7. The device of claim 1, further comprising a fluid-handling portion that defines a compartment coupled fluidically to the chamber by a flow path, wherein the channel and the opening form at least a portion of the flow path.

8. The device of claim 1, wherein the at least one thin-film layer includes a passivation layer of the at least one thin-film electronic device.

9. The device of claim 1, wherein the substrate is a semiconductor.

10. The device of claim 1, wherein the opening is of smaller diameter than the channel.

11. The device of claim 5, wherein the substrate has opposing surfaces, wherein the channel is formed in only one of the opposing surfaces, and wherein the plurality of thin-film layers is disposed above the only one opposing surface.

* * * * *